US008848282B2

(12) United States Patent
Islam

(10) Patent No.: US 8,848,282 B2
(45) Date of Patent: *Sep. 30, 2014

(54) SYSTEM AND METHOD FOR VOICE CONTROL OF MEDICAL DEVICES

(71) Applicant: Cheetah Omni, LLC, Ann Arbor, MI (US)

(72) Inventor: Mohammed N. Islam, Ann Arbor, MI (US)

(73) Assignee: Omni Medsci, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,678

(22) Filed: Jun. 10, 2013

(65) Prior Publication Data

US 2013/0274569 A1    Oct. 17, 2013

Related U.S. Application Data

(60) Continuation of application No. 13/349,244, filed on Jan. 12, 2012, now Pat. No. 8,472,108, which is a continuation of application No. 12/625,253, filed on Nov. 24, 2009, now Pat. No. 8,098,423, which is a division of application No. 12/206,432, filed on Sep. 8, 2008, now Pat. No. 7,633,673, which is a division of application No. 10/812,608, filed on Mar. 30, 2004, now Pat. No. 7,433,116, which is a continuation of application No. 10/757,341, filed on Jan. 13, 2004, now Pat. No. 7,259,906, which is a continuation of application No. 10/652,276, filed on Aug. 29, 2003, now abandoned.

(60) Provisional application No. 60/408,025, filed on Sep. 3, 2002.

(51) Int. Cl.
*H01S 3/00* (2006.01)

(52) U.S. Cl.
USPC ............................... 359/333; 600/424; 66/15

(58) Field of Classification Search
USPC .............................. 359/333; 600/424; 606/15
See application file for complete search history.

(56) References Cited

U.S. PATENT DOCUMENTS 4,063,106 A    12/1977  Ashkin et al.
4,158,750 A     6/1979  Sakoe et al.
(Continued)

FOREIGN PATENT DOCUMENTS

EP    1 148 666 A2    10/2001
WO    WO 97/15240     5/1997
(Continued)

OTHER PUBLICATIONS

Islam, M. N., et al., "Broad bandwidths from frequency-shifting solitons in fibers", Optics Letters, vol. 14, No. 7, pp. 370-372, Apr. 1, 1989.

(Continued)

*Primary Examiner* — Mark Hellner
(74) *Attorney, Agent, or Firm* — Brooks Kushman P.C.

(57) ABSTRACT

A light-based medical diagnostic system includes a plurality of semiconductor diodes with pump beams and a multiplexer capable of combining the pump beams and generating at least a multiplexed pump beam comprising one or more wavelengths. A first waveguide structure is configured to receive at least a portion of the one or more wavelengths and outputs a first optical beam. A second waveguide structure is configured to receive at least a portion of the first optical beam and to communicate at least the portion of the first optical beam to an output end of the second waveguide structure to form an output beam. A lens system is configured to receive at least a portion of the output beam and to communicate at least the portion of the output beam onto a part of a patient's body, such as a patient's blood.

20 Claims, 7 Drawing Sheets

(56) References Cited

U.S. PATENT DOCUMENTS

| | | | |
|---|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,267,256 A | 11/1993 | Saruwatari et al. |
| 5,267,323 A | 11/1993 | Kimura |
| 5,300,097 A | 4/1994 | Lerner et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,400,165 A | 3/1995 | Gnauck et al. |
| 5,408,409 A | 4/1995 | Glassman et al. |
| 5,458,122 A | 10/1995 | Hethuin |
| 5,544,654 A | 8/1996 | Murphy et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Montara et al. |
| 5,718,234 A | 2/1998 | Warden et al. |
| 5,747,806 A | 5/1998 | Khalil |
| 5,748,103 A | 5/1998 | Flach et al. |
| 5,792,204 A | 8/1998 | Snell |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,043,927 A | 3/2000 | Islam |
| 6,115,673 A | 9/2000 | Malin |
| 6,185,535 B1 | 2/2001 | Hedin et al. |
| 6,200,309 B1 | 3/2001 | Rice et al. |
| 6,224,542 B1 | 5/2001 | Chang et al. |
| 6,246,707 B1 | 6/2001 | Yin et al. |
| 6,246,896 B1 | 6/2001 | Dumoulin |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne |
| 6,289,238 B1 | 9/2001 | Besson et al. |
| 6,301,271 B1 | 10/2001 | Sanders et al. |
| 6,301,273 B1 | 10/2001 | Sanders et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,512,936 B1 | 1/2003 | Monfre |
| 6,543,012 B1 | 4/2003 | Viswanathan |
| 6,549,702 B2 | 4/2003 | Islam et al. |
| 6,567,431 B2 | 5/2003 | Tabirian et al. |
| 6,587,702 B1 | 7/2003 | Ruchti |
| 6,603,910 B2 | 8/2003 | Islam et al. |
| 6,605,080 B1 | 8/2003 | Altshuler et al. |
| 6,611,643 B2 | 8/2003 | Birk |
| 6,625,180 B2 | 9/2003 | Bufetov et al. |
| 6,631,025 B2 | 10/2003 | Islam et al. |
| 6,640,117 B2 | 10/2003 | Makarewicz |
| 6,659,947 B1 | 12/2003 | Carter et al. |
| 6,659,999 B1 | 12/2003 | Anderson et al. |
| 6,738,652 B2 | 5/2004 | Mattu |
| 6,760,148 B2 | 7/2004 | Islam |
| 6,773,922 B2 | 8/2004 | Jeng |
| 6,788,965 B2 | 9/2004 | Ruchti |
| 6,802,811 B1 | 10/2004 | Slepian |
| 6,816,241 B2 | 11/2004 | Grubisic |
| 6,847,336 B1 | 1/2005 | Lemelson |
| 6,864,978 B1 | 3/2005 | Hazen |
| 6,868,285 B2 * | 3/2005 | Muller-Dethlefs ........... 600/317 |
| 6,885,498 B2 | 4/2005 | Islam |
| 6,885,683 B1 | 4/2005 | Fermann et al. |
| 6,943,936 B2 | 9/2005 | Islam et al. |
| 6,990,364 B2 | 1/2006 | Ruchti |
| 7,010,336 B2 | 3/2006 | Lorenz |
| 7,027,467 B2 | 4/2006 | Baev et al. |
| 7,060,061 B2 | 6/2006 | Altshuler et al. |
| 7,098,992 B2 | 8/2006 | Ohtsuki et al. |
| 7,133,710 B2 | 11/2006 | Acosta |
| 7,167,300 B2 | 1/2007 | Fermann et al. |
| 7,209,657 B1 | 4/2007 | Islam |
| 7,233,816 B2 | 6/2007 | Blank |
| 7,259,906 B1 | 8/2007 | Islam |
| 7,263,288 B1 | 8/2007 | Islam |
| 7,294,105 B1 | 11/2007 | Islam |
| 7,299,080 B2 | 11/2007 | Acosta |
| 7,317,938 B2 | 1/2008 | Lorenz |
| 7,395,158 B2 | 7/2008 | Monfre |
| 7,433,116 B1 | 10/2008 | Islam |
| 7,456,965 B2 * | 11/2008 | Wang ........................ 356/369 |
| 7,519,253 B2 | 4/2009 | Islam |
| 7,519,406 B2 | 4/2009 | Blank |
| 7,620,674 B2 | 11/2009 | Ruchti |
| 7,633,673 B1 * | 12/2009 | Islam ........................ 359/333 |
| 7,697,966 B2 | 4/2010 | Monfre |
| 7,787,503 B2 | 8/2010 | Wadsworth |
| 7,787,924 B2 | 8/2010 | Acosta |
| 7,800,818 B2 | 9/2010 | Mattsson |
| 7,807,718 B2 | 10/2010 | Hashim |
| 7,949,017 B2 * | 5/2011 | Marciante et al. ................ 372/3 |
| 8,000,574 B2 | 8/2011 | Buchter |
| 8,098,423 B2 * | 1/2012 | Islam ........................ 359/333 |
| 8,145,286 B2 | 3/2012 | Arai |
| 8,472,108 B2 * | 6/2013 | Islam ........................ 359/333 |
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0058861 A1 | 5/2002 | Drew |
| 2002/0082612 A1 | 6/2002 | Moll et al. |
| 2002/0109621 A1 | 8/2002 | Khair et al. |
| 2002/0115914 A1 | 8/2002 | Russ |

(56) References Cited

U.S. PATENT DOCUMENTS

| | | | |
|---|---|---|---|
| 2002/0128846 | A1 | 9/2002 | Miller |
| 2002/0178003 | A1 | 11/2002 | Gehrke et al. |
| 2003/0022126 | A1 | 1/2003 | Buchalla |
| 2004/0174914 | A1 | 9/2004 | Fukatsu |
| 2004/0240037 | A1 | 12/2004 | Harter |
| 2005/0111500 | A1 | 5/2005 | Harter et al. |
| 2006/0013270 | A1 | 1/2006 | Yumoto et al. |
| 2006/0223032 | A1 | 10/2006 | Fried |
| 2006/0245461 | A1 | 11/2006 | Islam |
| 2006/0268393 | A1 | 11/2006 | Islam |
| 2007/0020181 | A1 | 1/2007 | Workman et al. |
| 2007/0078348 | A1 | 4/2007 | Holman |
| 2008/0105665 | A1 | 5/2008 | Kondo |
| 2009/0028193 | A1 | 1/2009 | Islam |
| 2009/0204110 | A1 | 8/2009 | Islam |
| 2010/0046067 | A1 | 2/2010 | Fermann et al. |
| 2010/0322490 | A1 | 12/2010 | Pan |
| 2010/0331637 | A1 | 12/2010 | Ting |
| 2011/0143364 | A1 | 6/2011 | Kim |
| 2012/0013722 | A1 | 1/2012 | Wong |

FOREIGN PATENT DOCUMENTS

| | | |
|---|---|---|
| WO | WO 97/49340 | 12/1997 |
| WO | WO 01/50959 A1 | 7/2001 |
| WO | WO 01/89362 A2 | 11/2001 |
| WO | WO 02/27640 A2 | 4/2002 |
| WO | WO 02/28123 A2 | 4/2002 |

OTHER PUBLICATIONS

Islam, M. N., et al., "Femtosecond distributed soliton spectrum in fibers", J. Opt. Soc. Am. B, vol. 6, No. 6, pp. 1149-1158, Jun. 1989.

Busse, Lynda E., et al., "Design Parameters for Fluoride Multimode Fibers", Journal of Lightwave Technology, vol. 9, No. 7, pp. 828-831, Jul. 1991.

Wüthrich, Stefan, et al., "Optical damage thresholds at 2.94 µm in fluoride glass fibers", Applied Optics, vol. 31, No. 27, pp. 5833-5837, Sep. 20, 1992.

Inoue, H., et al., "Computer simulation of the vibrational spectra and properties of fluoride glasses based on $ZrF_4$", Journal of Non-Crystalline Solids, vol. 161, pp. 118-122, 1993.

Mizunami, Toru, et al., "Gain saturation characteristics of Raman amplification in silica and fluoride glass optical fibers", Optics Communications 97, pp. 74-78, 1993.

Desthieux, B., et al., "111 kW (0.5 mJ) pulse amplification at 1.5 µm using a gated cascade of three erbium-doped fiber amplifiers," Appl. Phys. Lett. vol. 63, pp. 586-588, Aug. 2, 1993.

Edwards, Glenn, et al., "Tissue ablation by a free-electron laser tuned to the amide II band", Nature, vol. 371, pp. 416-419, Sep. 29, 1994.

Borrelli, N. F., et al., "Resonant and non-resonant effects in photonic glasses", Journal of Non-Crystalline Solids 185, pp. 109-122, 1995.

Asobe, Masaki, et al., "Third-order nonlinear spectroscopy in $As_2 S_3$ chalcogenide glass fibers", J. Appl. Phys. 77 (11), pp. 5518-5523, Jun. 1, 1995.

Jarman, Richard H., "Novel optical fiber lasers", Current Opinion in Solid State and Materials Science 1996, pp. 199-203, 1996.

Iatridis, James C., et al., "Is the Nucleus Pulposus a Solid or a Fluid? Mechanical Behaviors of the Nucleus Pulposus of the Human Intervertebral Disc", Spine, vol. 21(10), pp. 1174-1184, May 15, 1996.

Asobe, Masaki, "Nonlinear Optical Properties of Chalcogenide Glass Fibers and Their Application to All-Optical Switching", Optical Fiber Technology, vol. 3, Article No. OF970214, pp. 142-148, 1997.

Smektala, F., et al., "Chalcogenide glasses with large non-linear refractive indices", Journal of Non-Crystalline Solids 239, pp. 139-142, 1998.

Hamilton, James D., et al., "High Frequency Ultrasound Imaging with Optical Arrays", IEEE Transactions on Ultrasonics, Ferroelectrics, and Frequency Control, vol. 45, No. 1, pp. 216-235, Jan. 1998.

Hamilton, James D., et al., "High Frequency Ultrasound Imaging Using an Active Optical Detector", IEEE Transactions on Ultrasonics, Ferroelectrics, and Frequency Control, vol. 45, No. 3, pp. 719-727, May 1998.

Nowak, G. A., et al., "Low-power high-efficiency wavelength conversion based on modulational instability in high-nonlinearity fiber," Optics Letters, vol. 23, No. 12, pp. 936-938, Jun. 15, 1998.

Cardinal, T., et al., "Non-linear optical properties of chalcogenide glasses in the system As—S—Se", Journal of Non-Crystalline Solids 256 & 257, pp. 353-360, 1999.

Lucas, Jacques, "Infrared glasses", Current Opinion in Solid State & Materials Science 4, pp. 181-187, 1999.

Sanghera, J. S., et al., "Active and passive chalcogenide glass optical fibers for IR applications: a review", Journal of Non-Crystalline Solids 256 & 257, pp. 6-16, 1999.

Nishida, Yoshiki, et al., "Reliability of Fluoride Fiber Module for Optical Amplifier Use", IEEE Photonics Technology Letters, vol. 11, No. 12, pp. 1596-1598, Dec. 1999.

Nowak, George A., et al., "Stable supercontinuum generation in short lengths of conventional dispersion-shifted fiber", Applied Optics, vol. 38, No. 36, pp. 7364-7369, Dec. 20, 1999.

Urban, J. P. G., et al., "The Nucleus of the Intervertebral Disc from Development to Degeneration", Amer. Zool., vol. 40, pp. 53-61, 2000.

Hamilton, James D., et al., "High Frequency Optoacoustic Arrays Using Etalon Detection", IEEE Transactions on Ultrasonics, Ferroelectrics, and Frequency Control, vol. 47, No. 1, pp. 160-169, Jan. 2000.

Ranka, Jinendra K., et al., "Visible continuum generation in air-silica microstructure optical fibers with anomalous dispersion at 800 nm", Optics Letters, vol. 25, No. 1, pp. 25-27, Jan. 1, 2000.

Boult, Maggi, et al., "Systematic Review of Percutaneous Endoscopic Laser Discectomy: Update and Re-appraisal", Australian Safety and Efficacy Register of New Interventional Procedures—Surgical Report No. 5, 49 pages, Feb. 2000.

Boult, Maggi, et al., "Percutaneous Endoscopic Laser Discectomy", Systematic Review, Aust. N. Z. J. Surg., vol. 70, pp. 475-479, Apr. 7, 2000.

Camacho, Nancy P., et al., "FTIR Microscopic Imaging of Collagen and Proteoglycan in Bovine Cartilage," Biopolymers (Biospectroscopy), vol. 62, pp. 1-8, 2001.

Choi, Joon Y., et al., "Thermal, Mechanical, Optical, and Morphologic Changes in Bovine Nucleus Pulposus Induced by Nd:YAG ($\lambda = 1.32$ βm) Laser Irradiation", Lasers in Surgery and Medicine, vol. 28, pp. 248-254, 2001.

Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, pp. 33-37, 2001.

Jackson, Stuart D., et al., "Theory and numerical simulation of nth-order cascaded Raman fiber lasers", J. Opt. Soc. Am. B, vol. 18, No. 9, pp. 1297-1306, Sep. 2001.

Werle, Peter, et al., "Near- and mid-infrared laser-optical sensors for gas analysis", Optics and Lasers in Engineering 37, pp. 101-114, 2002.

Beck, Mattias, et al., "Continuous Wave Operation of a Mid-Infrared Semiconductor Laser at Room Temperature," Science, vol. 295, www.sciencemag.org, pp. 301-305, Jan. 11, 2002.

Harbold, J. M., et al., "Highly nonlinear As—S—Se glasses for all-optical switching", Optics Letters, vol. 27, No. 2, pp. 119-121, Jan. 15, 2002.

Coen, Stéphane, et al., "Supercontinuum generation by stimulated Raman scattering and parametric four-wave mixing in photonic crystal fibers", J. Opt. Soc. Am. B, vol. 19, No. 4, pp. 753-764, Apr. 2002.

Dudley, John M., et al., "Supercontinuum generation in air-silica microstructured fibers with nanosecond and femtosecond pulse pumping", J. Opt. Soc. Am. B, vol. 19, No. 4, pp. 765-771, Apr. 2002.

Harbold, Jeffrey M., et al., "Highly Nonlinear Ge—As—Se and Ge—As—S—Se Glasses for All-Optical Switching", IEEE Photonics Technology Letters, vol. 14, No. 6, pp. 822-824, Jun. 2002.

Husakou, Anton V., et al., "Supercontinuum generation, four-wave mixing, and fission of higher-order solitons in photonic-crystal fibers", J. Opt. Soc. Am. B, vol. 19, No. 9, pp. 2171-2182, Sep. 2002.

(56) References Cited

OTHER PUBLICATIONS

Wadsworth, William J., et al., "Supercontinuum generation in photonic crystal fibers and optical fiber tapers: a novel light source", J. Opt. Soc. Am. B, vol. 19, No. 9, pp. 2148-2155, Sep. 2002.
Kumar, V.V. Ravi Kanth, et al., "Extruded soft glass photonic crystal fiber for ultra broad supercontinuum generation", Optics Express, vol. 10, No. 25, pp. 1520-1525, Dec. 16, 2002.
Edwards, Glenn S., et al., "Advantage of the Mark-III FEL for biophysical research and biomedical applications", J. Synchrotron Rad. vol. 10, pp. 354-357, 2003.
Nicholson, J. W., et al., "Pulsed and continuous-wave supercontinuum generation in highly nonlinear, dispersion-shifted fibers", Applied Physics B 77, pp. 211-218, 2003.
Sobol, Emil, et al., "Time-resolved, light scattering measurements of cartilage and cornea denaturation due to free electron laser radiation", Journal of Biomedical Optics, vol. 8, No. 2, pp. 216-222, Apr. 2003.
Nicholson, J. W., et al., "All-fiber, octave-spanning supercontinuum", Optics Letters, vol. 28, No. 8, pp. 643-645, Apr. 15, 2003.
Faralli, S., et al., "Impact of Double Rayleigh Scattering Noise in Distributed Higher Order Raman Pumping Schemes", IEEE Photonics Technology Letters, vol. 15, No. 6, pp. 804-806, Jun. 2003.
"New and Emerging Techniques—Surgical, Rapid Review, Laser Discectomy", Australian Safety and Efficacy Register of New Interventional Procedures—Surgical, 12 pages, Jun. 2003.
Avdokhin, A. V., et al., "Continuous-wave, high-power, Raman continuum generation in holey fibers", Optics Letters, vol. 28, No. 15, pp. 1353-1355, Aug. 1, 2003.
Mussot, Arnaud, et al., "Generation of a broadband single-mode supercontinuum in a conventional dispersion-shifted fiber by use of a subnanosecond microchip laser", Optics Letters, vol. 28, No. 19, pp. 1820-1822, Oct. 1, 2003.
Slusher, Richard, et al., "Highly nonlinear composite chalcogenide/polymer fibers", OSA 2004, 1 page, 2004.
Thongtrangan, Issada, et al., "Minimally invasive spinal surgery: a historical perspective", Neurosurg. Focus, vol. 16, Article 13, pp. 1-10, Jan. 2004.
Hori, Takashi, et al., "Flatly broadened, wideband and low noise supercontinuum generation in highly nonlinear hybrid fiber", Optics Express, vol. 12, No. 2, pp. 317-324, Jan. 26, 2004.
Wadsworth, W. J., et al., "Supercontinuum and four-wave mixing with Q-switched pulses in endlessly single-mode photonic crystal fibres", Optics Express, vol. 12, No. 2, pp. 299-309, Jan. 26, 2004.
Hilligsoe, Karen Marie, et al., "Supercontinuum generation in a photonic crystal fiber with two zero dispersion wavelengths", Optics Express, vol. 12, No. 6, pp. 1045-1054, Mar. 22, 2004.
Venugopalan, V., "Optical Society of America BIOMED Topical Meeting Tutorial on Tissue Optics", pp. 1-32, Apr. 27, 2004.
Slusher, Richart E., et al., "Large Raman gain and nonlinear phase shifts in high-purity $As_2Se_3$ chalcogenide fibers", J. Opt. Soc. Am. B, vol. 21, No. 6, pp. 1146-1155, Jun. 2004.
Leon-Saval, S. G., et al., "Supercontinuum generation in submicron fibre waveguides", Optics Express, vol. 12, No. 13, pp. 2864-2869, Jun. 28, 2004.
Nicholson, J. W., et al., "High power, single mode, all-fiber source of femtosecond pulses at 1550 nm and its use in supercontinuum generation", Optics Express, vol. 12, No. 13, pp. 3025-3034, Jun. 28, 2004.
Genty, G., et al., "Enhanced bandwidth of supercontinuum generated in microstructured fibers", Optics Express, vol. 12, No. 15, pp. 3471-3480, Jul. 26, 2004.
Champert, Pierre-Alain, et al., "White-light supercontinuum generation in normally dispersive optical fiber using original multi-wavelength pumping system", Optics Express, vol. 12, No. 19, pp. 4366-4371, Sep. 20, 2004.
Nicholson, J. W., "Supercontinuum generation in ultraviolet-irradiated fibers", Optics Letters, vol. 29, No. 20, pp. 2363-2365, Oct. 15, 2004.
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, pp. 1969-1980, Nov. 2004.
Demircan, Ayhan, et al., "Supercontinuum generation by the modulation instability", Optics Communications 244, pp. 181-185, 2005.
Papernyi, S. B., et al., "Sixth-Order Cascaded Raman Amplification", OFC/NFOEC, 3 pages, 2005.
Tanaka, Keiji, "Optical nonlinearity in photonic glasses", Journal of Materials Science: Materials in Electronics 16, pp. 633-643, 2005.
Westbrook, Paul S., "Improved Supercontinuum Generation Through UV Processing of Highly Nonlinear Fibers", Journal of Lightwave Technology, vol. 23, No. 1, pp. 13-18, Jan. 2005.
Abeeluck, Akheelesh K., et al., "Continuous-wave pumping in the anomalous- and normal-dispersion regimes of nonlinear fibers for supercontinuum generation", Optics Letters, vol. 30, No. 1, pp. 61-63, Jan. 1, 2005.
Kutz, J. Nathan, et al., "Enhanced Supercontinuum Generation through Dispersion-Management", Optics Express, vol. 13, No. 11, pp. 3989-3998, May 30, 2005.
Lee, Ju Han, et al., "Experimental performance comparison for various continuous-wave supercontinuum schemes: ring cavity and single pass structures", Optics Express, vol. 13, No. 13, pp. 4848-4853, Jun. 27, 2005.
Saliminia, A., et al., "Ultra-broad and coherent white light generation in silica glass by focused femtosecond pulses at 1.5 $\mu m$", Optics Express, vol. 13, No. 15, pp. 5731-5738, Jul. 25, 2005.
Takushima, Yuichi, "High average power, depolarized super-continuum generation using a 1.55-$\beta m$ ASE noise source", Optics Express, vol. 13, No. 15, pp. 5871-5877, Jul. 25, 2005.
Travers, J. C., et al., "Extended continuous-wave supercontinuum generation in a low-water-loss holey fiber", Optics Letters, vol. 30, No. 15, pp. 1938-1940, Aug. 1, 2005.
Kobtsev, Serguei M., et al., "Modelling of high-power supercontinuum generation in highly nonlinear, dispersion shifted fibers at CW pump", Optics Express, vol. 13, No. 18, pp. 6912-6918, Sep. 5, 2005.
Falk, Peter, et al., "Supercontinuum generation in a photonic crystal fiber with two zero-dispersion wavelengths tapered to normal dispersion at all wavelengths", Optics Express, vol. 13, No. 19, pp. 7535-7540, Sep. 19, 2005.
Tombelaine, Vincent, et al., "Ultra wide band supercontinuum generation in air-silica holey fibers by SHG-induced modulation instabilities", Optics Express, vol. 13, No. 19, pp. 7399-7404, Sep. 19, 2005.
Lee, Ju Han, et al., "Continuous-wave supercontinuum laser based on an erbium-doped fiber ring cavity incorporating a highly nonlinear optical fiber", Optics Letters, vol. 30, No. 19, pp. 2599-2601, Oct. 1, 2005.
Genty, G., et al., "Supercontinuum generation in large mode-area microstructured fibers", Optics Express, vol. 13, No. 21, pp. 8625-8633, Oct. 17, 2005.
Schreiber, T., et al., "Supercontinuum generation by femtosecond single and dual wavelength pumping in photonic crystal fibers with two zero dispersion wavelengths", Optics Express, vol. 13, No. 23, pp. 9556-9569, Nov. 14, 2005.
Travers, J. C., et al., "Extended blue supercontinuum generation in cascaded holey fibers", Optics Letters, vol. 30, No. 23, pp. 3132-3134, Dec. 1, 2005.
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, pp. 91-93, Jan. 1, 2006.
Moon, Sucbei, et al., "Generation of octave-spanning supercontinuum with 1550-nm amplified diode-laser pulses and a dispersion-shifted fiber", Optics Express, vol. 14, No. 1, pp. 270-278, Jan. 9, 2006.
Fedotova, O., et al., "Supercontinuum generation in planar rib waveguides enabled by anomalous dispersion", Optics Express, vol. 14, No. 4, pp. 1512-1517, Feb. 20, 2006.
Harrington, James A., "Infrared Fiber Optics", OSA Handbook, vol. III, white paper, to be published by McGraw Hill, 13 pages, undated.
Aaviksoo, J., et al., "Observation of optical precursors at pulse propagation in GaAs", Physical Review A, vol. 44, No. 9, pp. R5353-R5356, Nov. 1, 1991.

(56) References Cited

OTHER PUBLICATIONS

Boppart, Stephen A., et al., "*Imaging developing neural morphology using optical coherence tomography*", Journal of Neuroscience Methods 70, pp. 65-72, 1996.

Boppart, Stephen A., et al., "*Noninvasive assessment of the developing Xenopus cardiovascular system using optical coherence tomography*", Proc. Natl. Acad. Sci. USA, vol. 94, pp. 4256-4261, Apr. 1997.

Tearney, Guillermo J., et al., "*In vivo Endoscopic Optical Biopsy with Optical Coherence Tomography*", Science, New Series, vol. 276, pp. 2037-2039, Jun. 27, 1997.

de Boer, Johannes F., et al., "*Imaging thermally damaged tissue by polarization sensitive optical coherence tomography*", Optics Express 212, vol. 3, No. 6, pp. 212-218, Sep. 14, 1998.

Roggan, André, et al., "*Optical Properties of Circulating Human Blood in the Wavelength Range 400-2500 NM*", Journal of Biomedical Optics, vol. 4, No. 1, pp. 36-46, Jan. 1999.

de Boer, Johannes F., et al., "*Determination of the depth-resolved Stokes parameters of light backscattered from turbid media by use of polarization-sensitive optical coherence tomography*", Optics Letters, vol. 24, No. 5, pp. 300-302, Mar. 1, 1999.

Rollins, Andrew M., et al., "*Real-time in vivo imaging of human gastrointestinal ultrastructure by use of endoscopic optical coherence tomography with a novel efficient interferometer design*", Optics Letters, vol. 24, No. 19, pp. 1358-1360, Oct. 1, 1999.

D'Amico, Anthony V., et al., "*Optical Coherence Tomography As a Method for Identifying Benign and Malignant Microscopic Structures in The Prostate Gland*", Basic Science, Urology 55 (5), pp. 783-787, 2000.

Li, Xingde, et al., "*Imaging needle for optical coherence tomography*", Optics Letters, vol. 25, No. 20, pp. 1520-1522, Oct. 15, 2000.

Oughstun, Kurt E., "*Influence of precursor fields on ultrashort pulse autocorrelation measurements and pulse width evolution*", Optics Express, vol. 8, No. 8, pp. 481-491, Apr. 9, 2001.

Kowalevicz, Andrew M., et al., "*Ultrahigh resolution optical coherence tomography using a superluminescent light source*", Optics Express 349, vol. 10, No. 7, pp. 349-353, Apr. 8, 2002.

Povazay, B., et al., "*Submicrometer axial resolution optical coherence tomography*", Optics Letters, vol. 27, No. 20, pp. 1800-1802, Oct. 15, 2002.

Xie, T.-Q., et al., "*Detection of tumorigenesis in urinary bladder with optical coherence tomography: optical characterization of morphological changes*", Optics Express, vol. 10, No. 24, pp. 1431-1443, Dec. 2, 2002.

Seefeldt, Michael, et al., "*Compact white-light source with an average output power of 2.4 W and 900 nm spectral bandwidth*", Optics Communications 216, pp. 199-202, 2003.

Wang, Yimin, et al., "*Ultrahigh-resolution optical coherence tomography by broadband continuum generation from a photonic crystal fiber*", Optics Letters, vol. 28, No. 3, pp. 182-184, Feb. 1, 2003.

Bizheva, K., et al., "*Compact, broad-bandwidth fiber laser for sub-2-µm axial resolution optical coherence tomography in the 1300-nm wavelength region,*" Optics Letters, vol. 28, No. 9, pp. 707-709, May 1, 2003.

Pan, Yingtian, et al., "*Hand-held arthroscopic optical coherence tomography for in vivo high-resolution imaging of articular cartilage*", Journal of Biomedical Optics 8(4), pp. 648-654, Oct. 2003.

Xie, Tuqiang, et al., "*Endoscopic optical coherence tomography with a modified microelectromechanical systems mirror for detection of bladder cancers*", Applied Optics, vol. 42, No. 31, pp. 6422-6426, Nov. 1, 2003.

Dubois, A., et al., "*Three-dimensional cellular-level imaging using full-field optical coherence tomography*", Physics in Medicine and Biology, Phys. Med. Biol. 49, pp. 1227-1234, 2004.

Park, Jesung, et al., "*Analysis of birefringent image in the retinal nerve fiber layer by polarization sensitive optical coherence tomography*", Ophthalmic Technologies XIV, Proceedings of SPIE, vol. 5314, pp. 188-194, 2004.

Unterhuber, A., et al., "*Advances in broad bandwidth light sources for ultrahigh resolution optical coherence tomography*", Physics in Medicine and Biology, Phys. Med. Biol. 49, pp. 1235-1246, 2004.

Drexler, Wolfgang, "*Ultrahigh-resolution optical coherence tomography*", Journal of Biomedical Optics, vol. 9, No. 1, pp. 47-74, Jan./Feb. 2004.

Schmitt, Joseph, et al., "*Intravascular Optical Coherence Tomography Opens a Window Onto Coronary Artery Disease*", Optics & Photonics News, pp. 20-25, Feb. 2004.

Nassif, N.A., et al., "*In vivo high-resolution video-rate spectral-domain optical coherence tomography of the human retina and optic nerve*", Optics Express, vol. 12, No. 3, pp. 367-376, Feb. 9, 2004.

Choi, Seung-Ho, et al., "*Observation of Optical Precursors in Water*", Physical Review Letters, vol. 92, No. 19, pp. 193903-1-193903-.3, May 14, 2004.

Pierce, Mark C., et al., "*Advances in Optical Coherence Tomography Imaging for Dermatology*", Optical Coherence Tomography Advances, The Journal of Investigative Dermatology, pp. 458-463, Sep. 3, 2004.

"State-Specific Trends in Chronic Kidney Failure—United States, 1990-2001", Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney . . . Feb. 12, 2010, pp. 918-920, Oct. 8, 2004.

I.B. Aris, A.A.E. Wagie, N.B. Mariun, A.B.E. Jammal, "An Internet-based blood pressure monitoring system for patients," Journal of Telemedicine and Telecare, pp. 51-53, 2001.

R.H. Istepanian, B. Woodward, P.A. Balos, S. Chen, B. Luk, "The comparative performance of mobile telemedical systems based on the IS-54 and GSM cellular telephone stanards," Journal of Telemedicine and Telecare, pp. 97-104, 1999.

Shaw, et al., IR Supercontinuum Generation in As—Se Photonic Crystal Fiber, Optical Society of America, 3 pages, © 2005.

PCT/US06/44451, Notification of Transmittal of the International Search Report and the Written Opinion of the International Searching Authority, or the Declaration, 12 pages, Date Mailed Nov. 29, 2007.

Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).

Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).

Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).

Borlinghaus, R.T., L. Kuschel, "White Light Laser: The Ultimate Source for Confocal Microscopy," http://www.leica-microsystems.com/science-lab/white-light-laser (Jun. 27, 2012).

Ziegler, U., A.G. Bittermann, M. Hoechli, "Introduction to Confocal Laser Scanning Microscopy (LEICA)," www.zmb.unizh.ch, May 29, 2013.

Hazen, K.H., M.A. Arnold, G.W. Small, "Measurement of glucose and other analytes in undiluted human serum with near-infrared transmission spectroscopy," Analytica Chimica Acta, vol, 371, pp. 255-267 (1998).

Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).

Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).

Troy, T.L., S.N. Thennadil, "Optical properties of human skin in the near infrared wavelength range of 1000 to 2200nm," Journal of Biomedical Optics, vol. 6, No. 2, pp. 167-176, (2001).

(56) References Cited

OTHER PUBLICATIONS

Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).

Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).

Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).

Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).

Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).

Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).

Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).

Kim-K.D. G.S. Son, S.S. Lim, S.S. Lee, "Measurement of glucose level exploiting a relative optical absorption at discrete probe wavelengths," Japanese Journal of Applied Physics, vol. 48, 077001 (2009).

Smith, J.L., "The Pursuit of Noninvasive Glucose: Hunting the Deceitful Turkey," 2nd Edition, pp. 1-141 (2011).

Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).

Lussi, A., R. Hibst, R. Paulus, "Diagnodent: An optical method for caries detection," Journal of Dental Research, vol. 83, special issue C, pp. C80-C83 (2004).

Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).

Zakian, C., I. Pretty, R. Ellwood, "Near-infrared hyperspectral imaging of teeth for dental caries detection," Journal of Biomedical Optics, vol. 16, No. 6, 064047 (2009).

Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).

Karlsson, L. "Caries detection methods based on changes in optical properties between healthy and carious tissue," International Journal of Dentistry, vol. 2010, Article ID 270729, 9 pages (2010).

Fried, D. M. Staninec, C.L. Darling, "Near-infrared imaging of dental decay at 1310nm," Journal of Laser Dentistry, vol. 18, No. 1, pp. 8-16 (2010).

Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).

Maia, A., L. Karlsson, W. Margulis, A. Gomes, "Evaluation of two imaging techniques: near-infrared transillumination and dental radiographs for the detection of early approximal enamel caries," Dentomaxillofacial Radiology, vol. 40, pp. 429-433 (2011).

Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).

Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).

Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).

Nishizawa, N., "Generation and application of high-quality supercontinuum sources," Optical Fiber Technology, vol. 18, pp. 394-402 (2012).

G.S. Edwards et al., "Free-electron-laser-based biophysical and biomedical instrumentation," American Institute of Physics, vol. 74, No. 7, pp. 3207-3245, Jul. 2003.

Computer Motion, Inc., "501(k) Summary—Zeus® MicroWrist™ Surgical System and Accessories," 6 pages, Sep. 24, 2002.

Computer Motion, Inc. "Hermes™ O.R. Control Center—510(k) Summary of Safety and Effectiveness," 5 pages, Oct. 11, 2002.

K.M. Joos, et al. "Optic Nerve Sheath Fenestration with a Novel Wavelength Produced by the Free Electron Laser (FEL)," Lasers in Surgery and Medicine, 27:191-205, 2000.

J. Sanghera, I. Aggarwal, "IR Fiber Optics at NRL," 10 pages, Undated.

J. Sanghera, L.B. Shaw, I.D. Aggarwal, "Applications of chalcogenide glass optical fibers," Academic of Science, pp. 1-11, 2003.

B. Rigas, P.T.T. Wong, "Human Colon Adenocarcinoma Cell Lines Display Infrared Spectroscopic Features," Cancer Research, pp. 84-88, Jan. 1, 1992.

G. Edwards, et al., "Comparison of OPA and Mark-III FEL for Tissue Ablation at 6.45 Microns," Department of Physics and Free Electron Laser Laboratory, Duke University, 7 pages, 2002.

Glenn Edwards, "Biomedical and potential clinical applications for pulsed lasers operating near 6.45 μm," Society of Photo-Optical Instrumentation Engineers, 2 pages, 1995.

Passat, "Solid-State Lasers and Optical Components," 5 pages, Jul. 14, 2003.

P.A. Thielen and L.B. Shaw, et al., "Small-core As—Se fiber for Raman amplification," Optics Letters, vol. 28, No. 16, 3 pages, Aug. 15, 2003.

R.Rox Anderson, et al., "Selective Photothermolysis: Precise Microsurgery by Selective Absorption of Pulsed Radiation," Department of Dermatology, Harvard Medical School, Science, vol. 220, 4 pages, Apr. 29, 1983.

U.S. Appl. No. 10/652,276, "System and Method for Voice Control of Medical devices," by Mohammed N. Islam, abandoned, Date Filed: Aug. 29, 2003.

U.S. Appl. No. 10/757,341, "System and Method for Voice Control of Medical devices," by Mohammed N. Islam, issued, Date Filed: Jan. 13, 2004.

U.S. Appl. No. 12/206,432, "System and Method for Voice Control of Medical Devices," by Mohammed N. Islam, pending, Filing Date: Sep. 8, 2008.

U.S. Patent and Trademark Office, Office Action for U.S. Appl. No. 12/206,432, filed Sep. 8, 2008, Mohammed N. Islam, Date Filed: Mar. 12, 2009.

U.S. Patent and Trademark Office, Notice of Allowance and Fee(s) Due for U.S. Appl. No. 12/206,432, filed Sep. 8, 2008, Mohammed N. Islam, Date Filed: Aug. 28, 2009.

Istepanian, Robert H., "The Comparative Performance of Mobile Telemedical Systems based on the IS-54 and GSM Cellular Telephone Standards"; Journal of Telemedicine and Telecare 1999; pp. 97-104.

Aris, Ishak Bin, "An Internet-Based Blood Pressure Monitoring System for Patients"; Journal of Telemedicine and Telecare 2001; pp. 51-53.

\* cited by examiner

SYSTEM AND METHOD FOR VOICE CONTROL OF MEDICAL DEVICES

CROSS-REFERENCE TO RELATED APPLICATIONS

This application is a continuation of U.S. patent application Ser. No. 13/349,244 filed Jan. 12, 2012, now U.S. Pat. No. 8,472,108 issued Jun. 25, 2013, which is a continuation of U.S. application Ser. No. 12/625,253 filed Nov. 24, 2009, now U.S. Pat. No. 8,098,423, issued Jan. 17, 2012, which is a divisional of U. S. patent application Ser. No. 12/206,432, filed Sep. 8, 2008, now U.S. Pat. No. 7,633,673, issued Dec. 15, 2009, which is a divisional of U.S. patent application Ser. No. 10/812,608, filed Mar. 30, 2004, now U.S. Pat. No. 7,433, 116, issued Oct. 7, 2008, which is a continuation of U. S. patent application Ser. No. 10/757,341, filed Jan. 13, 2004, now U.S. Pat. No. 7,259,906, issued Aug. 21, 2007, which is a continuation of U.S. patent application Ser. No. 10/652,276 filed Aug. 29, 2003, abandoned. Application Ser. No. 10/652, 276 claims the benefit to U.S. Provisional Patent Application No. 60/408,025 filed Sep. 3, 2002, the disclosures of which are incorporated in their entirety by reference herein.

TECHNICAL FIELD

This invention relates generally to medical devices and more particularly to a system and method for voice control of medical devices.

OVERVIEW

Medical procedures typically use medical instruments or devices that tend to require a high level of manual dexterity on the part of medical professionals. To achieve this high level of dexterity, medical professionals require years of training and practice. This high level of dexterity and the strain imposed on the medical professional when using those instruments can cause the medical professional to become fatigued during medical procedures. For example, certain medical instruments require the medical professional to use both hands and to stand next to the patient, sometimes in an awkward position through the entire procedure. This can create fatigue, thereby limiting the number of procedures that the medical professional is able to perform in a given period. In addition, the high level of fatigue may lead to unnecessary and dangerous errors occurring during medical procedures.

SUMMARY OF EXAMPLE EMBODIMENTS

In one embodiment, a light-based medical diagnostic system includes a pump source comprising a plurality of semiconductor diodes with pump beams, a multiplexer capable of combining the plurality of semiconductor diode pump beams and generating at least a multiplexed pump beam comprising one or more wavelengths, a first waveguide structure configured to receive at least a portion of the one or more wavelengths, wherein the first waveguide structure comprises at least in part a gain fiber and outputs a first optical beam, and a second waveguide structure configured to receive at least a portion of the first optical beam and to communicate at least the portion of the first optical beam to an output end of the second waveguide structure to form an output beam, wherein at least a portion of the output beam comprises at least one wavelength in the range of 1.7 microns or more. A lens system is configured to receive at least the portion of the output beam and to communicate at least the portion of the output beam through a patient's mouth onto a part of a patient's body comprising a patient's blood. In various embodiments, at least the portion of the output beam is adapted for use in medical diagnostics to measure a property of the patient's blood, wherein the medical diagnostics comprise a spectroscopic procedure comprising a differential measurement, wherein the differential measurement is based at least in part on a comparison of amplitudes at a plurality of associated wavelengths transmitted or reflected from the patient's blood.

In another embodiment, a light-based diagnostic system includes a pump source comprising a plurality of semiconductor diodes with pump beams, a multiplexer capable of combining the plurality of semiconductor diode pump beams and generating at least a multiplexed pump beam comprising one or more wavelength, first and second waveguide structures, and a lens system. The first waveguide structure is configured to receive at least a portion of the one or more wavelengths, wherein the first waveguide structure comprises at least in part a fused silica fiber, and outputs a first optical beam. The second waveguide structure is configured to receive at least a portion of the first optical beam and to communicate at least the portion of the first optical beam to an output end of the second waveguide structure to form an output beam. The lens system is configured to receive at least a portion of the output beam and to communicate at least the portion of the output beam through an orifice in a patient's body. In various embodiments, at least the portion of the output beam is adapted for use in multi-wavelength diagnostics to measure a property of a part of the patient's body, wherein the multi-wavelength diagnostics comprise a spectroscopic procedure comprising a differential measurement, wherein the differential measurement is based at least in part on a comparison of amplitudes at a plurality of associated wavelengths transmitted or reflected from the part of the patient's body.

In yet another embodiment, a light-based medical diagnostic system includes a pump source comprising a plurality of semiconductor diodes with pump beams and a multiplexer capable of combining the plurality of semiconductor diode pump beams and generating at least a multiplexed pump beam comprising one or more wavelengths. A first waveguide structure is configured to receive at least a portion of the one or more wavelengths, wherein the first waveguide structure comprises at least in part a fused silica fiber, and outputs a first optical beam. A second waveguide structure is configured to receive at least a portion of the first optical beam and to communicate at least the portion of the first optical beam to an output end of the second waveguide structure to form an output beam. A lens system is configured to receive at least a portion of the output beam and to communicate at least the portion of the output beam onto a part of a patient's body comprising a patient's blood.

In one embodiment, a medical device comprises an insertable portion capable of being inserted into an orifice associated with a body of a patient. The insertable portion comprising an automated head unit capable of being manipulated in at least two axes of motion based at least in part on one or more control signals. The medical device further comprises one or more controllers coupled to the automated head unit. In one particular embodiment, the one or more controllers generate the one or more control signals based at least in part on an input signal.

In another embodiment, a medical device capable of minimizing tissue damage comprises an insertable portion capable of being inserted into an orifice associated with a body of a patient. The medical device further comprises one or more sensors coupled to the insertable portion. The one or more sensors capable of generating a feedback signal capable of being used to substantially minimize damage to tissue associated with the patient.

In yet another embodiment, a medical device capable of being used in a medical procedure comprises a pump laser capable of generating a pump signal. The medical device further comprises a Raman wavelength shifter coupled to the pump laser, at least a portion of the wavelength shifter comprising a waveguide structure. In one particular embodiment, the Raman wavelength shifter generates an output optical signal comprising a wavelength of approximately 1.7 microns or more.

In still another embodiment, a medical device capable of being used in a medical procedure comprises a Raman wavelength shifter operable to generate an optical signal comprising a mid-infrared wavelength. At least a portion of the Raman wavelength shifter comprises a chalcogenide waveguide.

In another embodiment, a system for controlling a medical device includes a monitor capable of communicating medical information associated with a patient and a communication device capable of receiving one or more input signals from a user. In one particular embodiment, the one or more input signals are based at least in part on the medical information displayed on the monitor. The system further includes one or more processors coupled to the communicated device and operable to convert the one or more input signals into one or more control signals capable of being used to manipulate a medical device.

Depending on the specific features implemented, particular embodiments may exhibit some, none, or all of the following technical advantages. Various embodiments may be capable of reducing medical professional fatigue through the implementation of a control system capable of manipulating a medical device through voice commands. Some embodiments may be capable of controlling a medical device from a remote location. Other embodiments may be capable of reducing the level of dexterity required of a medical professional when performing a medical procedure.

Other technical advantages will be readily apparent to one skilled in the art from the following figures, description, and claims. Moreover, while specific advantages have been enumerated, various embodiments may include all, some, or none of the enumerated advantages.

BRIEF DESCRIPTION OF THE DRAWINGS

To provide a more complete understanding of the present invention and certain features and advantages, thereof, reference is made to the following description taken in conjunction with the accompanying drawings, in which.

DESCRIPTION OF EXAMPLE EMBODIMENTS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
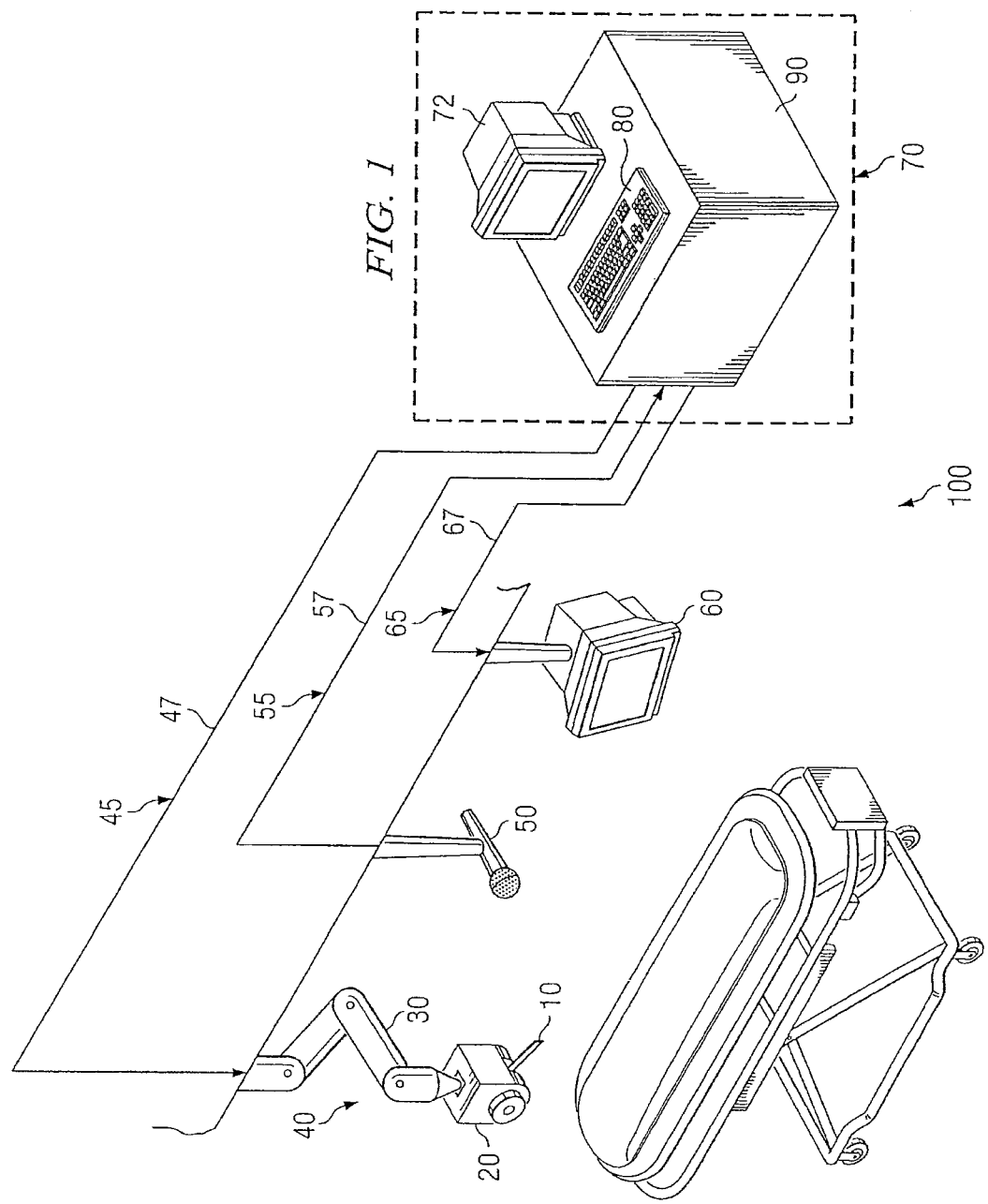
FIG. 1 illustrates one example embodiment of a medical device control system.

FIG. 1 illustrates one example embodiment of a medical device control system 100. In this example, system 100 includes a medical device 10, a manipulator 40, a microphone 50, a display device 60, and a host 70. In various embodiments, system 100 may be capable of receiving voice commands associated with the manipulation of medical device 10 from a medical professional, such as a nurse, a medical assistant, a medical technician, and/or a doctor. In some cases, system 100 is capable of assisting a medical professional during a medical procedure by processing data signals associated with one or more voice commands and manipulating medical device 10 in response to those commands.

Medical device 10 may comprise any device or instrument that a medical professional needs to perform a medical procedure. Medical device 10 can comprise, for example, a surgical scalpel, a scope, a laser, an imaging device, a microscope, or a combination of these or any other suitable device. As used throughout this document, the term "scope" refers to any medical device capable of entering a patient's body, such as endoscopes, colonoscopes, gastroscopes, enteroscopes, bronchoscopes, laryngoscopes, choledochoscopes, sigmoidoscopes, duodenoscopes, arthoroscopes, cystoscopes, hyteroscopes, laparoscopes, or a combination of these or any other suitable device.

In one particular embodiment, medical device 10 comprises an endoscope. In those cases, the endoscope may comprise an insertable portion capable of being inserted through an orifice associated with a patient. In other embodiments, the insertable portion may be capable of being guided through the patient's orifice, and capable of collecting biological samples from the patient for investigation. The orifice associated with the patient may comprise, for example, a throat, a mouth, a nasal passage, an orifice created by the medical professional, and/or any other suitable orifice. In some embodiments, medical device 10 may include a fiber-optic cable with a lens system at the end that is capable of sending images to a camera and/or a display device, such as display device 60.

In other embodiments, medical device 10 may comprise one or more sensors coupled to feedback control circuitry that is capable of minimizing collateral tissue damage during a medical procedure. In various embodiments, the one or more sensors and the control circuitry may be capable of providing positioning information to a medical professional and/or a controller, such as system controller 90. In other embodiments, the one or more sensors and the control circuitry may be capable of providing data associated with one or more physiological parameters associated with the patent to a medical professional and/or a controller. In some cases, the one or more sensors may be capable of detecting and/or alerting a medical professional or a controller when medical device 10 is in close proximity to and/or in contact with tissue. In other cases, the one or more sensors and the control circuitry may be capable of detecting when medical device 10 is in contact with tissue and capable of overriding control signals received by medical device 10.

In this example, manipulator 40 includes an actuation unit 20 and a supporting structure 30. Actuation unit 20 may house one or more control systems capable of receiving control signals and manipulating medical device 10 in response to those control signals. The one or more control systems may comprise, for example, a mechanical control system, an electrical control system, or a combination of these or any other control system. As used throughout this document, the phrase "mechanical control system" refers to a control system that at least partially includes mechanical components. In various embodiments, actuation unit 20 can implement a mechanical control system, such as a hydraulic system, pneumatic system, or a pulley guidewire system.

Supporting structure 30 may comprise a robotic arm, one or more pivoted links, multiple links connected together to move in a "scissor-like" manner, or any other structure capable of supporting and manipulating medical device 10. Although this example depicts manipulator 40 and medical device 10 as separate devices, manipulator 40 and medical device 10 can comprise a unitary medical apparatus capable of performing the desired functionalities without departing from the scope of the present disclosure. For example, manipulator 40 and medical device 10 can be combined to form a unitary medical apparatus, such as an endoscope, have an automated portion.

In some embodiments, a freedom of motion associated with manipulator 40 can have a resolution that substantially replicates the manual dexterity of a medical professional and/or a manual medical device used by the medical professional. In some cases, manipulator 40 may have a step size and/or angle of rotation step size that is substantially similar to the manual dexterity of a medical professional and/or a manual medical device used by the medical professional. For example, the number of degrees of manipulation freedom associated with medical device 10 can match the number of degrees of manipulation freedom currently available on manual devices. That is, if a conventional manual device that has four degrees of freedom in the x-y plane, then the range of motion associated with manipulator 40 can include at least four degrees of freedom in the x-y plane. In some embodiments, manipulator 40 may include manual override controls that allow a medical professional to exercise manual control of medical device 10.

Manipulator 40 is coupled to host 70 through a first communication link 45. As used throughout this document, the term "couple" and or "coupled" refers to any direct or indirect communication between two or more elements, whether or not those elements are in physical contact with one another. In this example, first communication link 45 is operable to facilitate the communication of command/data signals 47 between manipulator 40 and host 70. Command/data signals 47 may comprise, for example, video signals from a video device coupled to medical device 10, data obtained by sensors coupled to medical device 10, or manipulation commands generated in response to voice commands, auxiliary input commands, and/or automated commands.

In this example, host 70 is capable of performing a desired communicating and/or computing functionality. For example, host 70 may be capable of at least partially contributing to the manipulation of medical device 10. In other embodiments, host 70 may be capable of collecting, entering, processing, storing, retrieving, amending, and/or dispatching medical data during a medical procedure. In operation, host 70 may execute with any of the well-known MS-DOS, PC-DOS, OS-2, MAC-OS, WINDOWS™, UNIX, or other appropriate operating systems. In some embodiments, host 70 may include a graphical user interface (GUI) 72 that enables a medical professional to display medical data and/or medical video associated with medical device 10. Host 70 may comprise, for example, a desktop computer, a laptop computer, a server computer, a personal digital assistant, and/or any other computing or communicating device or combination of devices.

In this example, host 70 includes system controller 90 capable of processing, collecting, storing, retrieving, and/or amending medical data and/or video during a medical procedure. System controller 90 may comprise one or more computers, an embedded microprocessor, or any other appropriate device or combination of devices capable of processing and/or generating voice command signals 47 and/or 57. In operation, system controller 90 may execute with any of the well-known MS-DOS, PC-DOS, OS-2, MAC-OS, WINDOWS™, UNIX, or other appropriate operating systems. In this embodiment, system controller 90 may implement voice recognition software operable to process voice command signals 57. For example, system controller 90 may implement one or more voice recognition software programs, such as ViaVoice or Dragon Speech Recognition software, or any appropriate proprietary or nonproprietary voice recognition software. In certain embodiments, the voice recognition software may be programmed to recognize the medical professional's voice and commands may be customized to the medical professional's preferences. In addition, the voice recognition software may be capable of filtering out background noise.

System controller 90 is operable to process voice command signals 57, generate command/data signals 47 in response to the voice command, and communicate the command/data signals 47 to manipulator 40. System controller 90 may also be used to collect and record data using a memory storage device. System controller 90 may be operable to provide data associated with a patient's medical status during a medical procedure to the medical professional using display device 60 and/or GUI 72, or any other appropriate devices.

In this embodiment, host 70 also includes an auxiliary input device 80 coupled to system controller 90. Although a keyboard is depicted in this example, any other device capable of inputting commands and/or data may be used without departing from the scope of this disclosure. In this example, auxiliary device 80 is operable to facilitate manual entry of manipulation commands to supplement and/or replace voice commands. In addition, the medical professional may use auxiliary device 80 to input data into system controller 90, such as the patient's physiological parameters, for example, blood pressure, heart rate, blood oxygen level, or to retrieve data stored in a memory device associated with host 70.

In this example, system 100 also includes display device 60 and a graphical user interface (GUI) 72, each capable of displaying medical information, such as medical data and/or medical video. Display device 60 and GUI 72 may comprise, for example, a monitor, a LED, a heads-up display, virtual reality goggles, a closed circuit television, a CAVE environment, or any other device or combination of devices capable of displaying. In some cases, display device 60 and GUI 72 may display a live video image from a video device associated with medical device 10, information about a patient's medical status, such as the current state of any number of the patient's physiological parameters, information about the particular medical device 10 being used, or any other information that may assist a medical professional during a medical procedure. In this example, display device 60 is coupled to host 70 through a third communication link 65, which is operable to facilitate the communication of data signals 67 to and/or from host 70.

In this example, system 100 also includes communication device 50 that enables a medical professional to communicate with host 70. Communication device 50 can comprise any device that enables a medical professional to communicate with host 70. Communication device 50 may comprise, for example, a telephone, a wireless device, a voice-over-IP device, a unidirectional microphone attached to a headset worn by a medical professional, a bi-directional microphone, or any other suitable communicating device or combination of devices. Communication device 50 may be selectively attached to and/or placed near the medical professional for ease of use. Attaching communication device 50 to the medical professional can, in some cases, advantageously minimize background noise. Although system 100 includes one communication device 50 in this example, any other number of communication devices may be used without departing from the scope of the present disclosure. Communication device 50 is coupled to host 70 through a second communication link 55, which is operable to facilitate the communication of voice command signals 57 between communication device 50 and host 70.

In the illustrated embodiment, system 100 includes at least a first communications link 45, a second communications link 55, and a third communications link 65 each operable to facilitate the communication of data to and/or from host 70. Communications links 45, 55, and 65 may include any hardware, software, firmware, or combination thereof. In various embodiments, communications link 45, 55, and 65 may comprise any communications medium capable of assisting in the communication of analog and/or digital signals. Communications links 45, 55, and 65 may, for example, comprise a twisted-pair copper telephone line, a fiber optic line, a Digital Subscriber Line (DSL), a wireless link, a USB bus, a PCI bus, an Ethernet interface, or any other suitable interface operable to assist in the communication of information to and/or from network 104.

In conventional medical procedures involving a scope, a medical professional manually manipulates the medical device based on feedback from the medical device. The medical professional typically uses one hand to hold the medical device and guide it into and through a patient's body. The medical professional's other hand is used to manipulate the manual controls of the medical device. Thus, conventional systems typically require significant manual dexterity, which can result in a significant amount of strain on the medical professional.

Unlike conventional procedures, system 100 comprises a communication device 50 that enables a medical professional to manipulate medical device 10 using voice commands, auxiliary input commands, and/or automated commands. Allowing a medical professional to use voice commands and/or automated commands can significantly reduce the manual dexterity, and the resulting strain, imposed on the medical professional during a medical procedure.

In operation, a medical professional can speak voice commands into communication device 50 for communication to host 70. Host 70 receives voice command signals 57 from communication device 50 and processes those signals using a voice recognition module associated with host 70. Host 70 converts the voice command signals into command/data signals 47 and communicates signals 47 to manipulator 40. Manipulator 40 responds by causing medical device 10 to perform its desired function. Voice commands may comprise, for example, a voice to take a photograph of a portion of the patient's body, a voice command to change an image size by zooming in or out, or any other suitable voice command capable of causing medical device 10 to perform its functionality. In other embodiments, host 70 is capable of automatically generating command/data signals 47 based at least in part on data received from medical device 10 through communication link 47.

Figure 2:
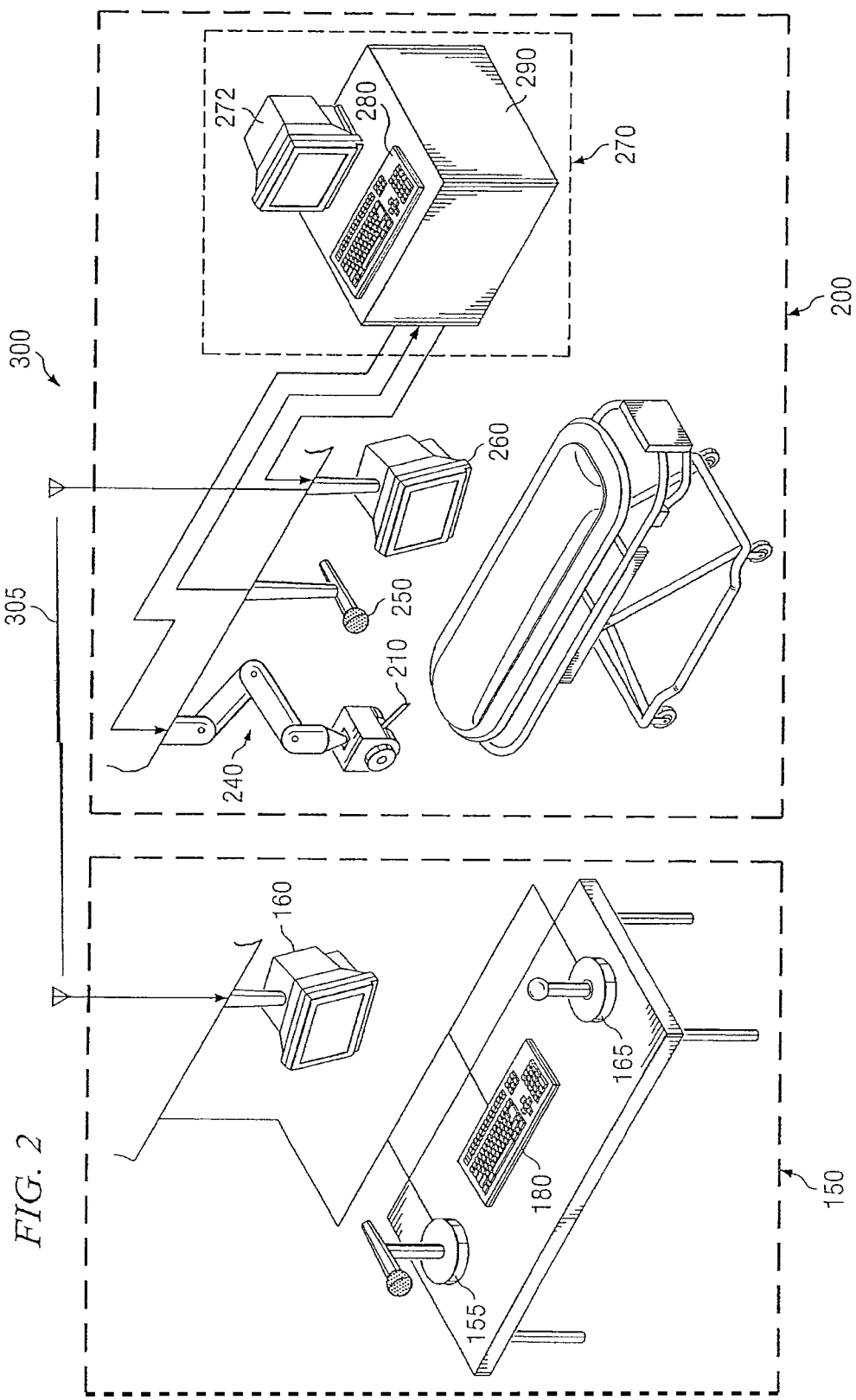
FIG. 2 illustrates another example embodiment of a medical device control system.

FIG. 2 illustrates another example embodiment of a medical device control system 300. System 300 includes system 150 for remote manipulation of a medical device 210 and system 200 for voice control of medical device 210. In this example, system 150 is capable of controlling at least a portion of system 200 from a remote location. For example, a medical professional may use system 150 to remotely control system 200 in the case where the medical professional is not located near system 200. The remote location may comprise, for example, a different location in the hospital that includes system 200, a location in a different hospital, or any other location.

System 150 can include a communication device 155, a display device 160, a first auxiliary input device 165, and a second auxiliary input device 180. The structure and function of communication device 155, display device 160, and second auxiliary input device 180 can be substantially similar to the structure and function of communication device 50, display device 60, and auxiliary input device 80, respectively, of FIG. 1. First auxiliary input device 165 may comprise, for example, a joystick, a computer mouse, a rollerball, knobs, levers, buttons, touchpads, touchscreens, or any other appropriate control device capable of being used to control manipulator 240. In this example, a medical professional can use first auxiliary input device 165 to control manipulator 240 from the remote location.

In this embodiment, system 200 includes a medical device 210, a manipulator 240, a communication device 250, and a display device 260. System 200 also includes a host 270 comprising GUI 272, a third auxiliary input device 280, and a system controller 290. Although host 270 resides within system 200 in this example, host 270 could reside within system 150 or could reside in any location accessible to system 300 without departing from the scope of the present disclosure. The structure and function of medical device 210, manipulator 240, communication device 250, display device 260, host 270, GUI 272, third auxiliary input device 280, and system controller 290 can be substantially similar to the structure and function of medical device 10, manipulator 40, communication device 50, display device 60, host 70, GUI 72, auxiliary input device 80, and system controller 90, respectively, of FIG. 1.

System 150 communicates with system 200 over communication link 305. Although communication link 305 comprises a single communication link in this example, any other number of communication links may be used without departing from the scope of the present disclosure. Communications link 305 may include any hardware, software, firmware, or combination thereof. In various embodiments, communications link 305 may comprise a communications medium capable of assisting in the communication of analog and/or digital signals. Communications link 305 may, for example, comprise a twisted-pair copper telephone line, a fiber optic line, a Digital Subscriber Line (DSL), a wireless link, a USB bus, a PCI bus, an Ethernet interface, or a combination of these or other elements.

In some embodiments, a first medical professional can manually insert medical device 210 into a patient. In those cases, system 200 can communicate data to a second medical professional using remote system 150 through communication link 305. The second medical professional, while monitoring display device 160, can remotely manipulate medical device 210 using voice instructions communicated through communication device 155 coupled to communication link 305 to host 270. In this manner, the medical professional using system 150 can substantially emulate a medical professional's manual control of medical device 210. In other embodiments, the medical professional can remotely manipulate medical device 210 using auxiliary devices 165 and/or 180. In an alternative embodiment, a medical professional can insert medical device 210 into a patient using system 200 locally or using system 150 remotely.

In addition to voice command control and/or auxiliary input device control, other methods of medical device control may be implemented. In some cases, system 150 and/or system 200 can implement a heads-up-display (HUD) capable of controlling and/or manipulating medical device 210 and/or manipulator 240. The HUD may be capable of projecting images onto or near the eyes of a medical professional and capable of sending command signals using a virtual control device attached to the medical professional. In another example, the medical professional may wear a helmet capable of manipulating medical device 210 and/or manipulator 240 based at least in part on command signals generated in response to a motion associated with the head of the medical professional. For example, rotation of the head to the right may indicate that the operator wants the medical device to move to the right.

Figure 3:
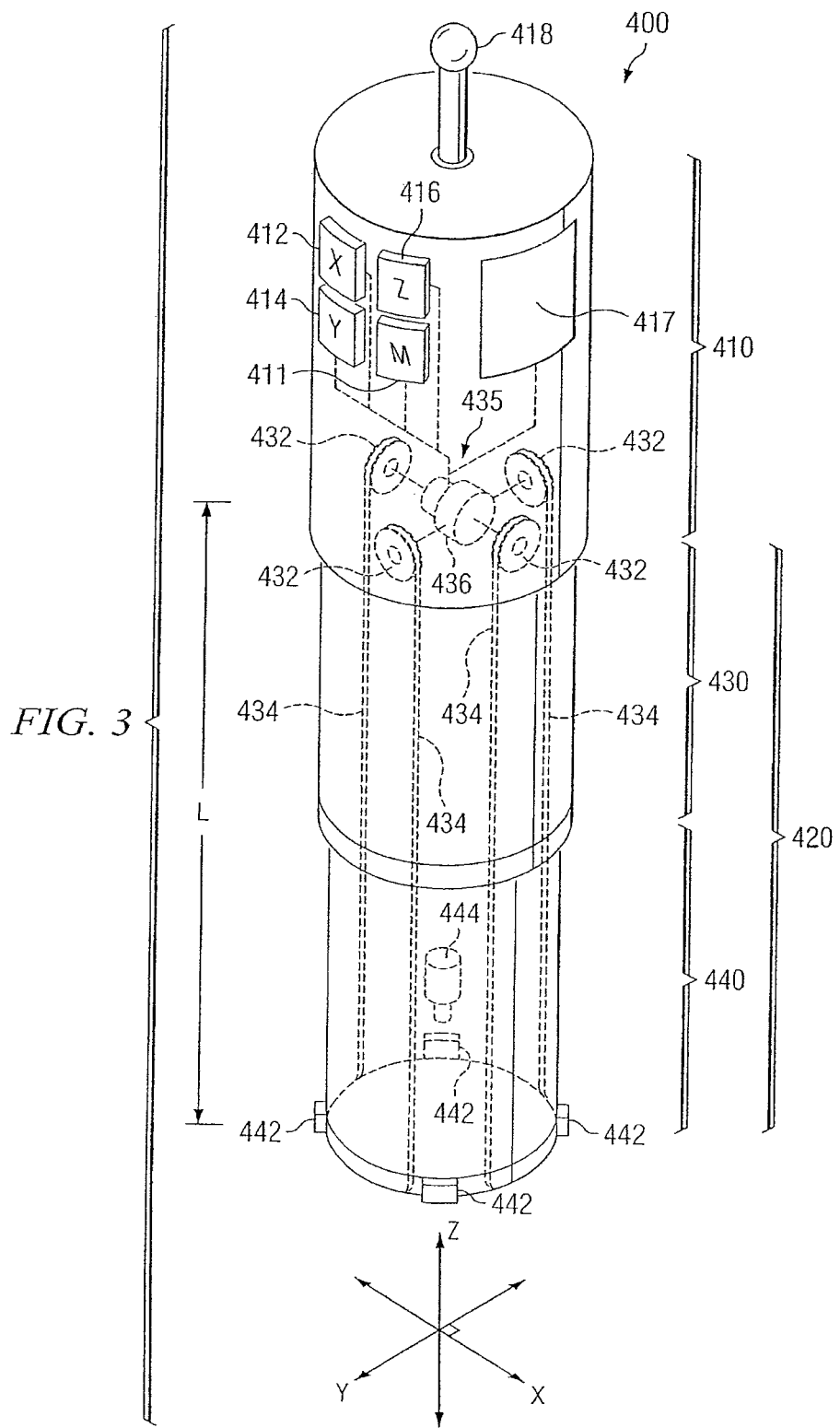
FIG. 3 illustrates an example medical device capable of being inserted into a patient's body during a medical procedure.

FIG. 3 illustrates an example medical device 400. In various embodiments, at least a portion of medical device 400 may be inserted into a patient's body through an orifice during a medical procedure. The orifice may comprise, for example, the patient's throat or mouth, the patient's nasal passages, an incision made during surgery, or any other suitable orifice. In this particular example, medical device 400 comprises a scope. The scope may comprise, for example, an endoscope, a colonoscope, a gastroscope, a enteroscope, a bronchoscope, a laryngoscope, a choledochoscope, a sigmoidoscope, a duodenoscope, a arthoroscope, a cystoscope, a hyteroscope, a laparoscope, or a combination of these or any other suitable device. In various embodiments, medical device 400 can be controlled through, for example, voice commands, auxiliary input command, automated commands, and/or manual commands. In some cases, medical device 400 can be coupled to a medical device control system, such as system 100 or system 300 of FIG. 1 and FIG. 2, respectively.

Medical device 400 includes a base portion 410 capable of controlling and/or at least partially contributing to the manipulation of an insertable portion 420. In this example, base portion 410 includes control system 435 capable of at least partially contributing to the control and/or the manipulation of insertable portion 420. Control system 435 may be capable of receiving, processing, executing, and/or communicating one or more signals associated with the manipulation of insertable portion 420. In various embodiments, these signals received by base portion 410 may comprise, for example, voice commands, auxiliary input commands, automated commands, physiological parameters, video data, positioning data, or a combination of these or other signal types.

In various embodiments, control system 435 may reside in a location outside of base portion 410 and/or may be partially or wholly included within base portion 410. Control systems 435 may comprise, for example, a mechanical control system, an electrical control system, an electro-mechanical control system, or a combination of these or any other suitable control system. The phrase "mechanical control system" refers to a control system that at least partially includes mechanical components. Mechanical control systems can include, for example, hydraulic components, pneumatic components, pulleys, guidewires, gears, actuators, pushrods, sprocket/chain mechanisms, feedback control circuitry, or any other suitable components.

In this particular embodiment, control system 435 includes a manual override control module 411, an x-axis control module 412, a y-axis control module 414, and a z-axis control module 416. Control modules 411, 412, 414, and 416 may include any hardware, software, firmware, or combination thereof. In some embodiments, control modules 411, 412, 414, and 416 may comprise buttons, knobs, dials, control circuitry, or any other suitable control input device. In this particular embodiment, control modules 412, 414, and 416 operate to receive and process input signals from a medical professional. In addition, control modules 412, 414, and 416 operate to at least partially contribute to the manipulation of insertable portion 420. The input signals may comprise, for example, voice commands, auxiliary input commands, and/or manual input commands. In other embodiments, control modules 412, 414, and 416 operate to receive and process input signals from a host and/or system controller. For example, a medical professional can use control modules 412, 414, and 416 to individually control medical device 400 in the x-, y-, and z-axes, respectively. In various embodiments, override control module 411 may be capable of enabling the medical professional to override the automatic operation of medical device 400 as necessary during a medical procedure.

Control system 435 may also include touch-screen 417 and controller 418. Controller 418 operates to combine the individual control functions of control modules 412, 414, and 416 into a single controller. For example, a medical professional can use controller 418 and/or touchscreen 417 to manually control medical device 400 in the x-, y-, and z-axes, respectively. Controller 418 can comprise any device capable of controlling the manipulation of insertable portion 420. Controller can comprise, for example, a joystick, a rollerball, knobs, levers, buttons, or any other appropriate control device.

Control system 435 further includes motors 436, pulleys 432, and guidewires 434. Although motors, pulleys, and guidewires are used in this example, control system 435 can include any other components capable of contributing to the manipulation of insertable portion 420 without departing from the scope of the present disclosure. In this example, motors 436 operate to control the positioning of insertable portion 420 based at least in part on control signals received from modules 411, 412, 414, and 416, and/or controller 418. Motors 436 operate to manipulate guidewires 434 coupled to one end of insertable portion 420. In other embodiments, base unit 410 includes actuators, pushrods, sprocket/chain mechanisms, feedback control circuitry, or any other control mechanism appropriate to control insertable portion 420.

In this example, pulleys 432 and motors 436 operate to control the tension in guidewires 434. In some embodiments, each guidewire 434 may comprise two or more segments, each segment comprising a different radial stiffness. For example, a first segment of guidewire 434 may be coupled to a pulley 432, and a second segment of guidewire 434 may be coupled to an end of insertable portion 420. In that example, the second segment of guidewire segment may have a radial stiffness that is less than a radial stiffness associated with the first segment guidewire. In various embodiments, the force exerted by guidewires 434 can cause insertable portion 430 to move in a corresponding manner.

Medical device 400 may also include insertable portion 420 connected to base portion 410 and capable of being inserted into an orifice or incision in a patient's body during a medical procedure. In this particular embodiment, a medical professional can, using base portion 410, manipulate insertable portion 420 in the patient's body to perform a medical procedure. In various embodiments, a medical professional can control insertable portion 420 using voice commands, auxiliary input commands, automated commands, and/or manually.

In this example, insertable portion 420 includes a flexible portion 430 and an automated head unit 440. In this particular embodiment, one end of each guidewire 434 is connected to one end of automated head unit 440, while the other end of each guidewire 434 is connected to one of pulleys 432. Although pulleys and guidewires are used to manipulate automated head unit 440, any other appropriate control mechanism may be used without departing from the scope of the present disclosure. In this example, control system 435 operates to create tension in guidewires 434. The tension in guidewires 434 operates to exert a force on automated head unit 440, which causes automated head unit 440 to move in a corresponding manner. For example, control system 435 may operate to apply tension to one or more guidewires 434 creating a force in the x-plane, which causes automated head unit 440 to move in the x-plane. Any suitable movement of automated head unit 440 in the x-y plane tends to impart a corresponding movement to flexible portion 430 in the x-y plane.

In this example, four guidewires 434 are used to manipulate automated head unit 440 with two guidewires 434 connected along the x-axis and two guidewires 434 connected along the y-axis. In an alternative embodiment, six or more guidewires 434 may be positioned around the periphery of the insertable portion 420, which can allow a medical professional more precise control of medical device 400. In some cases, the movement of automated head unit 440 may be controlled independently of the movement of flexible portion 430. In some embodiments, flexible portion 430 and automated head unit 440 may operate as "telescoping" tubes, where automated head unit 440 may retract into and extend from flexible portion 430 to adjust a length (L) of insertable portion 420. Such a telescoping motion may be controlled through the positioning of pulleys 432 and guidewires 434.

In this particular embodiment, control modules 412, 414, and/or 416 receive and process command signals corresponding to a desired manipulation of insertable portion 420. Control module 412 and control module 414 are operable to control the motion of automated head unit 440 and the entire insertable portion 420 in the x-axis and y-axis, respectively. In some embodiments, control module 416 is operable to adjust the distance that automated head unit 440 moves relative to flexible portion 430. In those cases, control module 416 is operable to cause motor 436 to position the pulleys 432 and guidewires 434 so as to extend and retract automated head unit 440 relative to flexible portion 430. Control module 412 and control module 414 are operable to independently control the motion of automated head unit 440 regardless of length L, enabling insertable portion 420 to have independent motion in the x-, y-, and z-axes.

Insertable portion 420 may also include sensors 442 and a camera 444. Although this example depicts sensors 442 as being connected to automated head unit 440, sensors may be connected to any portion of medical device 400 without departing from the scope of the present disclosure. Injury may occur when a medical professional accidentally or mistakenly causes insertable portion 420 to contact tissue associated with the patient, which can cause bruising or damage to the tissue. Sensors 442 can comprise any device capable of providing data and/or a signal to a medical professional. Sensors 442 may be capable of generating and transmitting, for example, positioning information associated with insertable portion 420, physiological information associated with the patient, control signals, a signal indicating the presence or absence of blood, or any other data. In one particular embodiment, sensors 442 are capable of generating and transmitting data associated with insertable portion's 420 proximity to tissue of the patient.

In other embodiments, sensors 442 may be capable of detecting a collision with tissue. In those cases, sensors 442 are capable of generating and transmitting a feedback signal to control modules 412, 414, 416, a host coupled to medical device 400, or a system controller coupled to medical device 400. For example, sensors 442 may communicate data indicating that wall tissue of a patient's orifice has been encountered and that device 400 may need to be directed away from that wall to prevent injury to the patient's tissue. In some embodiments, sensors 442 operate to generate alarms associated with medical device 400. For example, one or more sensors 442 may monitor the presence of blood in the orifice, so that the medical professional may be alerted to unexpected or excessive bleeding.

In operation, medical device 400 may be inserted into the patient by inserting insertable portion 420 into the appropriate orifice or incision. In some embodiments, a medical professional can insert medical device 400 into the patient. In other embodiments, the insertion of medical device 400 into the patient may be performed using a medical device control system implementing a manipulator, such as system 100 and manipulator 40 of FIG. 1 or system 300 and manipulator 240 of FIG. 2.

In this particular embodiment, medical device 400 is capable of being manipulated in at least three axes of motion. That is, medical device 400 is capable of being manipulated in the x-axis, y-axis, and z-axis. In other embodiments, medical device 400 is capable of being manipulated in at least two axes of motion. In some embodiments, medical device 400 may be capable of manipulating insertable portion 420 one axis at a time. In other embodiments, medical device 400 may be capable of manipulating insertable portion 420 one axis at a time and manipulating insertable portion 420 along multiple axes substantially simultaneously. In this example, medical device 400 is capable of manipulating insertable portion 420 along multiple axes substantially simultaneously. As used throughout this document, the phrase, "substantially simultaneously" refers to the manipulation of insertable portion 420 and/or automated head unit 440 in multiple axes in response to an input command before responding to a subsequent input command. For example, medical device 400 can manipulate insertable portion 420 along the z-axis and, during that manipulation, medical device 400 can also manipulate insertable portion 420 along the x-axis. In various embodiments, medical device 400 can manipulate automated head unit 440 independently of the movement of flexible portion 430.

Figure 4:
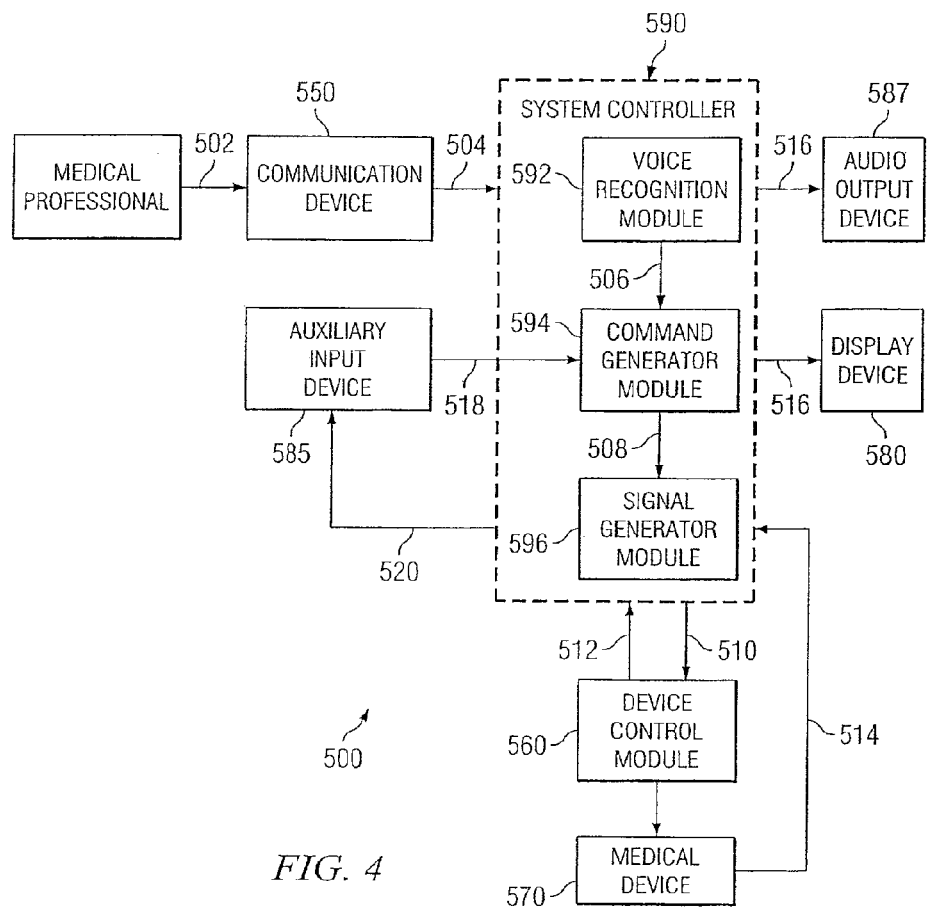
FIG. 4 is a block diagram illustrating a flow of command signals from a medical professional to a medical device in a medical device control system.

FIG. 4 is a block diagram illustrating a flow of command signals from a medical professional to a medical device in a medical device control system 500. In various embodiments, medical device control system 500 can be substantially similar to control system 100 of FIG. 1 or control system 300 of FIG. 2. In this example, a communication device 550 receives a voice command 502 from a medical professional. In various embodiments, the structure and function of communication device 550 can be substantially similar to the structure and function of communication device 50 of FIG. 1. Communication device 550 operates to convert voice command 502 into an electrical voice command signal 504 and to communicate electrical voice command signal 504 to a system controller 590. In various embodiments, the structure and function of system controller 590 can be substantially similar to the structure and function of system controller 90 of FIG. 1.

In this particular embodiment, system controller 590 comprises a voice recognition module 592 capable of at least partially contributing to one or more functions of system controller 590. That is, voice control module 592 is not required to be capable of performing the desired functionality of system controller 590 alone, but may contribute to the performance of the function as part of a larger routine. In this example, voice recognition module 592 at least partially contributes to the conversion of voice command signal 504 to a control signal 506. Voice recognition module 592 may include any hardware, software, firmware, or any combination thereof that is capable of converting voice command signal 504 into control signal 506.

System controller 590 also includes a command generator module 594 capable of at least partially contributing to one or more functions of system controller 590. In this example, command generator module 594 operates to receive control signal 506 communicated from voice recognition module 592 and at least partially contributes to the conversion of control signal 506 into a command signal 508. Command generator 594 may comprise any hardware, software, firmware, or any combination thereof that is capable of converting control signal 506 into command signal 508. In this example, command generator module 594 communicates command signal 508 to a signal generator module 596 capable of at least partially contributing to one or more functions of system controller 590. In this example, signal generator module 596 at least partially contributes to the conversion of command signal 508 into an actuation signal 510. Signal generator 596 may comprise any hardware, software, firmware, or any combination thereof that is capable of converting command signal 508 into actuation signal 510.

In this example, system controller 590 communicates actuation signal 510 to a device control module 560 capable of manipulating a medical device 570. In various embodiments, the structure and function of device control module 560 can be substantially similar to the structure and function of actuation unit 20 of FIG. 1 or base portion 410 of FIG. 3. In various embodiments, the structure and function of medical device 570 can also be substantially similar to the structure and function of medical device 10 of FIG. 1 or medical device 400 of FIG. 3.

In various embodiments, device control module 560 may be capable of generating a feedback signal 512 and communicating feedback signal 512 to system controller 590. Feedback signal 512 may comprise, for example, positioning data associated with medical device 570, a video feed, a physiological parameter associated with a patient, or any other information associated with medical device 570, device control module 560, and/or a patient undergoing a medical procedure. In some embodiments, medical device 570 can communicate data 514 to system controller 590. Data 514 may comprise, for example, positioning data, one or more physiological parameters associated with a patient, a live video feed associated with a camera coupled to medical device 570, or any other data capable of being collected by medical device 570.

In various embodiments, system controller 590 may be capable of generating commands on its own based at least in part on data 514 and/or feedback signal 512 communicated from medical device 570 and/or device control module 560. For example, if medical device 570 comprises a scope with blood sensors, system controller 590 may stop the movement of the scope within a patient's body if data 514 is received from medical device 570 indicating that the patient is bleeding excessively.

In this example, system 500 also includes a display device 580 capable of displaying data associated with medical device 570 and/or a patient. The structure and functional of display device 580 can be substantially similar to the structure and function of display device 60 or GUI 72 of FIG. 1. Although system 500 includes a single display device in this example, any other number of display devices may be used without departing from the scope of the present disclosure. In some embodiments, system controller 590 can communicate an output signal 516 containing data associated with medical device 570 and/or a patient to display device 580.

In some embodiments, system 500 may also include an audio output device 587 capable of communicating data associated with medical device 570 and/or a patient. Audio output device 587 can comprise any device capable of providing an audio output signal, such as a speaker, headphones, an audio alarm device, or any other suitable audio output device. Although system 500 includes a single audio output device in this example, any other number of audio output devices may be used without departing from the scope of the present disclosure. In some embodiments, system controller 590 may communicate an audio output signal 516 to output device 587 so that the medical professional may receive the data associated with output signal 516 in audio format.

Although, in most cases, voice command 502 represents the primary control input into system 500, system 500 also includes an auxiliary input device 585 capable of generating a control signal 518. Control signal 518 can comprise data that is substantially similar to data contained within control signal 506. In various embodiments, the structure and function of auxiliary input device 585 can be substantially similar to the structure and function of auxiliary input devices 165 or 180 of FIG. 2. Although system 500 includes a single auxiliary input device in this example, any other number of auxiliary input devices may be used without departing from the scope of the present disclosure. In this particular embodiment, auxiliary input device 585 is coupled directly to command generator 594. In some embodiments, auxiliary input device 585 may also receive data signals 520 from system controller 590. For example, in a case where auxiliary input device 585 comprises a "force-feedback" joystick, signals 520 may comprise the feedback signal representing the force being exerted on medical device 570 by the patient's body.

Figure 5:
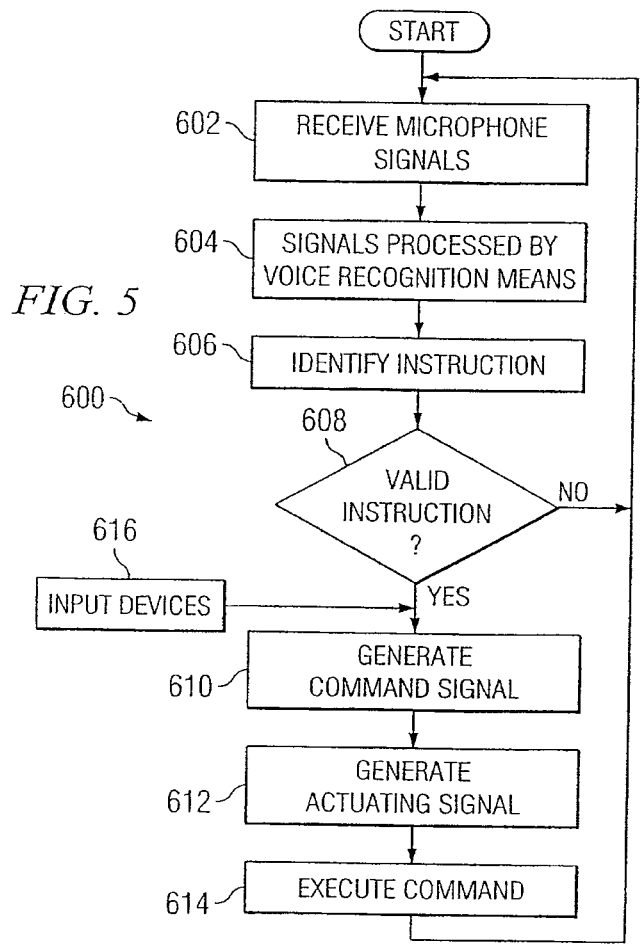
FIG. 5 is a flow chart illustrating an exemplary method for processing a voice control signal and/or a command signal received by a medical device control system.

FIG. 5 is a flow chart illustrating an exemplary method 600 for processing a voice control signal and/or a command signal received by a medical device control system. In one particular embodiment, voice control signals and/or command signals are received from system 100 of FIG. 1. Although system 100 is used in this example, any other system, such as systems 300 and 500 of FIGS. 2 and 4, respectively, may be used without departing from the scope of the present disclosure.

In this example, method 600 begins at step 602 where communication device 50 receives a voice command from a medical professional. Communication device 50 operates to convert the voice command into voice command signal 57 and communicates voice command signal 57 to host 70. In this particular example, host 70 includes a voice recognition module that processes voice command signal 57 at step 604 by converting voice command signal 57 into a control signal. In various embodiments, the structure and function of the voice recognition module can be substantially similar to voice recognition module 592 of FIG. 4. In this example, the voice recognition module further operates to identify the specific voice command represented by the control signal at step 606. In some embodiments, identifying the specific voice command may be accomplished by comparing the received control signal with a list of pre-programmed commands stored in a memory device associated with host 70.

The voice recognition module validates the control signal at step 608. If the voice command is not recognized as a pre-programmed command, the invalid voice command is ignored and the method loops back to step 602. If the voice command is valid, the voice recognition module communicates the control signal to a command generator. In this example, the command generator operates to convert the control signal into a command signal representing the voice command at step 610. In various embodiments, the structure and function of the command generator can be substantially similar to the structure and function of command generator module 594 of FIG. 4.

In an alternate embodiment, auxiliary control signals capable of manipulating a medical device may be generated by an auxiliary input device at step 616. In various embodiments, the auxiliary input device may comprise, for example, auxiliary input devices 165 and/or 180 of FIG. 2. The auxiliary input device communicates the auxiliary control signal to the command generator, which converts the auxiliary control signal into a command signal at step 610. The command generator also operates to communicate the command signal to a signal generator.

In this example, the signal generator operates to convert the command signal into an actuation signal 47 representing the voice command of the medical professional at step 612. In various embodiments, the structure and function of the signal generator can be substantially similar to the structure and function of signal generator module 596 of FIG. 4. In this example, manipulator 40 and/or medical device 10 operates to receive and execute actuation signal 47 at step 614.

Medical devices, such as a scope, that are adapted to be inserted into the patient's body typically permit the introduction of a waveguide structure or other wired device through the patient's orifice. The waveguide structure can comprise, for example, an optical fiber, a hollow tube waveguide, an air core waveguide, a planar waveguide, or a combination of these or other devices. Examples of such additional devices include, for example, surgical knives, sample collectors, and/or cauterizing heads. In some cases, inserting a waveguide structure may enable, for example, the early detection of cancerous cells and may contribute to the removal of the cancerous cells. In various embodiments, the waveguide structure may communicate an optical signal wavelength of 1.7 microns or more.

In some embodiments, a waveguide structure may be implemented in a medical device that uses an optical signal wavelength in the mid-infrared (mid-IR) wavelength range to perform surgery and/or spectroscopy on a patient. In various embodiments, a wavelength in the mid-IR range comprises a wavelength between approximately two (2) microns and approximately ten (10) microns. In other embodiments, a wavelength in the mid-IR range comprises a wavelength between approximately five (5) and seven (7) microns. For light-based surgery and spectroscopy, it can be particularly advantageous to use an optical signal wavelength in the range between approximately 5 microns to approximately 7 microns to minimize tissue damage or collateral damage. In a particular embodiment, an optical signal having a wavelength of approximately 6.45 microns may be advantageously used for light-based surgery and/or spectroscopy.

In some embodiments, a Raman wavelength shifter coupled to a pump laser is capable of generating an optical signal wavelength in the mid-IR range. As used in this document, the phrase "Raman wavelength shifter" refers to any device that uses the Raman effect to shift a shorter optical signal wavelength to a longer optical signal wavelength. The Raman wavelength shifters may comprise, for example, one or more reflectors, one or more gratings, an optical fiber, or a combination of these or other elements. In various embodiments, the Raman wavelength shifter may comprise, for example, a chalcogenide glass fiber that is capable of shifting the shorter pump laser wavelength to a longer wavelength, such as a wavelength in the mid-IR region. The chalcogenide fiber may comprise, for example, a ZBLAN fiber, a sulphide fiber, a selenides fiber, or a telluride fiber, or a combination of these or other fiber types.

In other embodiments, a first wavelength shifter coupled to a pump laser may be capable of shifting an optical signal wavelength to approximately 2 microns. The first wavelength shifter may comprise, for example, a fused silica optical fiber capable of shifting the shorter pump laser wavelength to approximately two (2) microns. In that example, a second Raman wavelength shifter is coupled to the first Raman wavelength shifter and is capable of shifting the two (2) micron signal to a wavelength in the five (5) to seven (7) micron range. In that example, the second Raman wavelength shifter comprises a chalcogenide glass fiber.

Figure 6A:
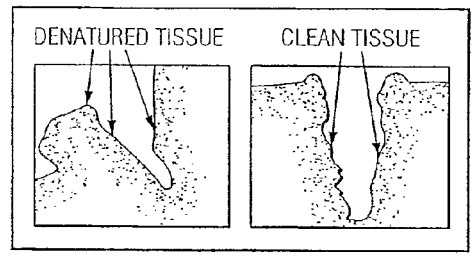
FIG. 6A compares a surgical incision made using a 2.94 micron optical signal wavelength to a surgical incision made using a 6.45 micron optical signal wavelength.

FIG. 6A compares a surgical incision made using a 2.94 micron optical signal wavelength to a surgical incision made using a 6.45 micron optical signal wavelength. This figure illustrates that tissue damage, such as denatured tissue, can result when a medical device implements a 2.94 micron optical signal wavelength. This tissue damage tends to result from the protein temperatures in the tissue do not uniformly exceed the water temperature in the aqueous components of the tissue.

Compared to the incision performed using the 2.94 micron optical signal wavelength, the incision made using the 6.45 micron optical signal has little or no denatured tissue. This reduction in collateral tissue damage is based at least in part on the tissue's ability to absorb differential energy. For example, when using an optical signal wavelength at approximately 6.45 microns to create an incision, the protein temperatures in the tissue uniformly exceed the water temperature in the tissue and the protein begins to transform into brittle denatured protein. The brittle fracture of the proteins at the onset of explosive vaporization leads to the confinement of collateral damage. Therefore, the use of a 6.45 micron optical signal wavelength as a tissue cutting implement may minimize collateral tissue damage during laser-based surgery. By using an optical signal wavelength of 6.45 microns with a medical scope-type device, "clean" surgery may be performed for many medical procedures, such as removing cancerous polyps. Similar results can be obtained using an optical signal wavelength in the five (5) to seven (7) micron range.

Figure 6B:
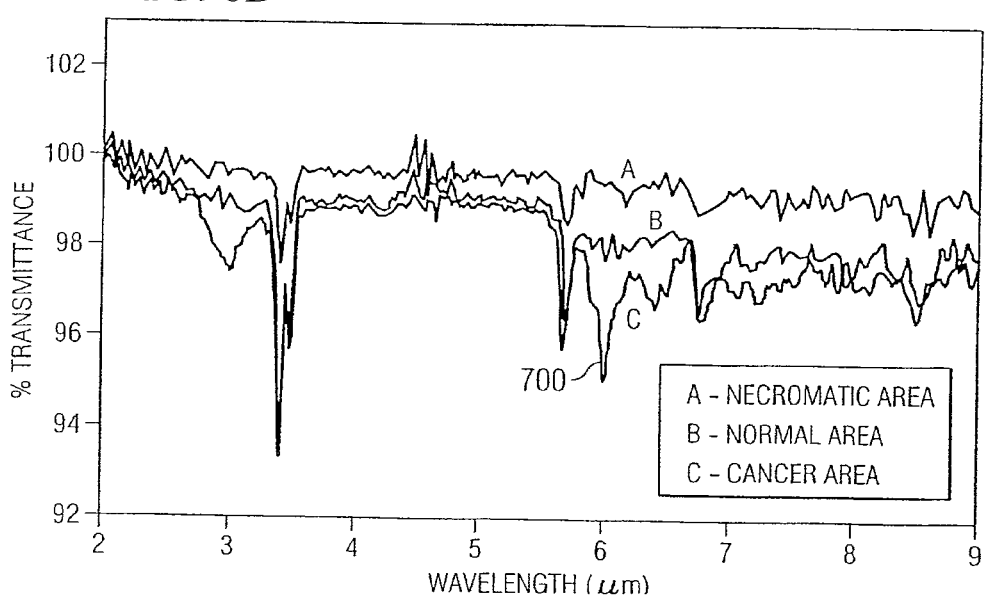
FIG. 6B illustrates example evanescent spectra in different cell-type regions.

FIG. 6B illustrates example evanescent spectra in different cell-type regions (using a mouse as the biological sample). This figure illustrates that cancerous cells tend to show a distinct reduction 700 in transmission at an optical signal wavelength of approximately 6.1 microns. Medical professionals can exploit this spectral signature in various medical procedures, such as a procedure for the early detection of cancer. Thus, an optical signal wavelength in the mid-IR range may be used to perform a medical procedure for the early detection of tissue abnormalities such as cancer cells. In other embodiments, an optical signal wavelength in the mid-IR range can be used in a diagnostic procedure, such as spectroscopy. Diagnostic techniques capable of using the mid-IR optical signal wavelength include, for example, transmission, reflection, fluorescence, and near field microscopy. Although specific examples of spectroscopy are discussed, any other appropriate form of spectroscopy may be used without departing from the scope of this disclosure.

To improve the signal-to-noise ratio of a spectroscopic measurement such as in FIG. 6B, several methodologies may be used. First, a differential measurement may be taken between a known cancer-free area and the suspect area, for example, differential spectroscopy rather than absolute spectroscopy. In addition, measurements may be taken at several wavelengths and compared to each other. For example, measuring the differential transmission of the tissue at two or more wavelengths, such as 5 microns and 6.1 microns, may: improve the signal-to-noise ratio of the cancer cell signature.

Figure 7:
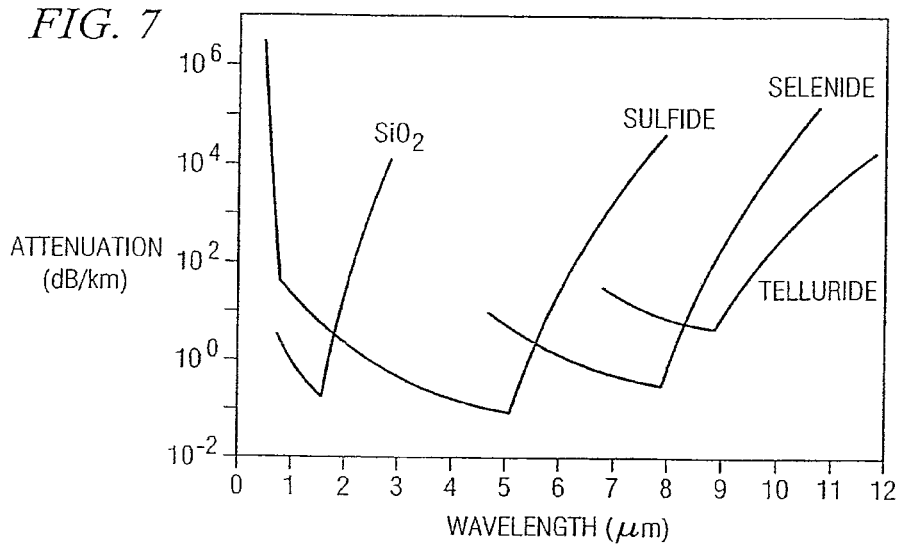
FIG. 7 illustrates example attenuation characteristics of several optical fibers based on wavelength.

FIG. 7 illustrates example attenuation characteristics of several optical fibers based on wavelength. This example shows that fused silica ($SiO_2$) fibers become lossy above approximately 2 microns in wavelength, while mid-IR optical fibers remain relatively loss-less above 2 microns. A mid-IR fiber may comprise any optical fiber capable of at least partially transmitting for at least a portion of the mid-IR range. For example, a mid-IR fiber may comprise a chalcogenide fiber, such as a sulfide fiber, a selenides fiber, or a telluride fiber. Therefore, in some cases, a pump source coupled to a medical device, such as medical device 400 of FIG. 3, may comprise a high powered pump source coupled to a Raman wavelength shifter comprising a mid-IR fiber. In a particular embodiment, such a pump source may operate in a pulsed mode or in a continuous wave mode. The power levels required depend on the particular application. For example, spectroscopy may require a relatively low power level, while surgery may require a relatively high power level.

Conventional surgical devices capable of using a 5.0 to 6.5 micron optical signal wavelength typically implement a Free Electron Laser (FEL) pump source. However, a FEL pump source is a large and very expensive facility that tends to be impractical for surgical applications. Unlike conventional surgical devices, a medical device, such as device 400 of FIG. 3, can include a pump laser coupled to one or more Raman wavelength shifters capable of shifting a shorter signal wavelength to a longer signal wavelength. In that example, at least a portion of the Raman wavelength shifter can be implemented in a waveguide structure. In various embodiments, the longer signal wavelength can comprise, for example, an optical signal wavelength in the mid-IR wavelength range. Coupling a pump laser to one or more Raman wavelength shifters can result in a commercially and economically viable optical cutting implement for use in a medical device. In addition, coupling a pump laser to one or more Raman wavelength shifters can result in a significantly smaller footprint area than a FEL pump source and can significantly reduce the cost.

Conventional wavelength shifters or oscillators are typically implemented in fused silica fiber. The loss associated with fused silica fiber tends to increase rapidly for optical signal wavelengths greater than about 2 or 2.3 microns. Unlike conventional wavelength shifters, a medical device, such as device 400 of FIG. 3, can include a Raman wavelength shifter or oscillator that is capable of transmitting in the mid-IR wavelength range, such as chalcogenide optical fibers.

FIGS. 8A through 8D are block diagrams illustrating example embodiments of Raman wavelength shifters and/or Raman oscillators capable of shifting a shorter pump signal wavelength to a longer output signal wavelength. Although particular examples of wavelength shifters are described in FIGS. 8A through 8D, any other Raman wavelength shifter can be implemented without departing from the scope of the present disclosure.

Figure 8A:
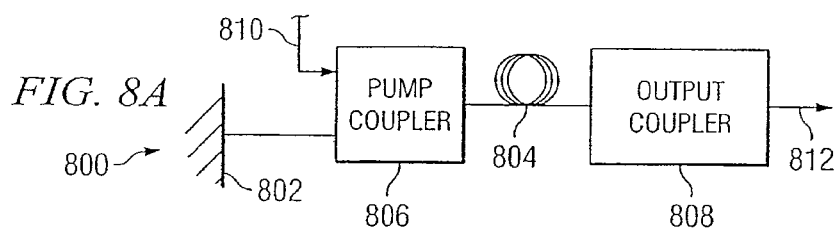
FIGS. 8A through 8D are block diagrams illustrating example embodiments of Raman wavelength shifters and/or Raman oscillators capable of shifting a pump signal to an output signal wavelength of 1.7 microns or more.

FIG. 8A is a block diagram illustrating one example of a Raman wavelength shifter 800 capable of shifting a shorter pump signal 810 wavelength to a longer output signal wavelength 812. In this example, Raman wavelength shifter 800 operates to generate an optical signal wavelength 812 of 1.7 microns or more. In various embodiments, Raman wavelength shifter 800 can operate to generate an optical signal wavelength 812 in the mid-IR wavelength range. In other embodiments, Raman wavelength shifter 800 can operate to generate an optical signal wavelength 812 a wavelength in the five (5) to seven (7) micron range. In various embodiments, pump signal 810 can comprise, for example, a 1310 nanometer (nm) wavelength, 1390 nm wavelength, 1510 nm wavelength, or other optical signal wavelength.

Raman wavelength shifter includes a gain fiber 804 operable to facilitate shifting pump signal 810 to a desired wavelength. Gain fiber 804 may comprise any waveguide structure capable of wavelength shifting pump signal 810 to a longer wavelength or a different Raman cascade order. In this particular embodiment, gain fiber 804 comprises an optical fiber. The optical fiber used as gain fiber 804 may comprise, for example, a dispersion compensating fiber, a dispersion shifter fiber, a single mode fiber, a chalcogenide fiber, a fused silica optical fiber, or a combination of these or other fiber types. Raman wavelength shifter 800 also includes a broadband reflector 802 operable to substantially reflect all optical signal wavelengths contained within Raman wavelength shifter 800 and a pump signal coupler 806. Reflector 802 may comprise any device capable of reflecting a wide range of wavelength signals, such as a mirror. Pump signal coupler 806 may comprise any device capable of coupling pump signal 810 to Raman wavelength shifter 800, such as a wavelength division multiplexer or a power coupler.

In this example, Raman wavelength shifter 800 further includes a wavelength separator 808 capable of transmitting at least a portion of the desired wavelength from Raman wavelength shifter 800. In addition, wavelength separator 808 operates to at least partially reflect a desired wavelength to gain medium 804 to continue lasing at the desired wavelength or wavelengths. In this particular embodiment, a cavity is formed between reflector 802 and wavelength separator 808. Separator 808 could comprise, for example, a demultiplexer, one or more partially transmissive gratings, one or more partially transmitting mirrors, one or more Fabry Perot filters, one or more dielectric gratings, or any combination of these or other devices.

Figure 8B:
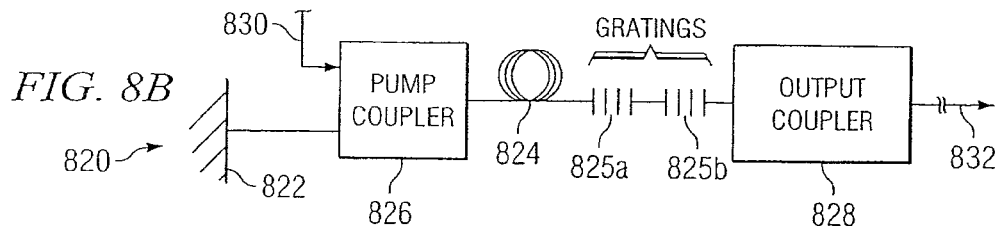

FIG. 8B is a block diagram illustrating one example of a Raman wavelength shifter 820 capable of shifting a shorter pump signal 830 wavelength to a longer output signal wavelength 832. In this example, Raman wavelength shifter 820 operates to generate an optical signal wavelength 832 of 1.7 microns or more. In various embodiments, Raman wavelength shifter 820 operates to generate an optical signal wavelength 832 in the mid-IR wavelength range. In other embodiments, Raman wavelength shifter 820 operates to generate an optical signal wavelength 832 a wavelength in the five (5) to seven (7) micron range. In various embodiments, pump signal 830 can comprise, for example, a 1310 nanometer (nm) wavelength, 1390 nm wavelength, 1510 nm wavelength, or other optical signal wavelength.

In this example, Raman wavelength shifter 820 includes a reflector 822, a gain fiber 824, a pump input coupler 826, and a wavelength separator 828. In various embodiments, the structure and function of reflector 822, gain fiber 824, coupler 826, and separator 828 can be substantially similar to reflector 802, gain fiber 804, coupler 806, and separator 808 of FIG. 8A, respectively. In this particular embodiment, at least a portion of gain fiber 824 can comprise a chalcogenide fiber.

Raman wavelength shifter 820 may also include at least a first selecting element 825a and a second selecting element 825b. Although this example may also include two selecting elements 825a and 825b, any number of selecting elements can be used without departing from the scope of the present disclosure. Selecting elements 825a and 825b can comprise any device, such as a dielectric grating or one or more Fabry Perot filters. Each selecting element operates to transmit a portion of a desired wavelength to be output from Raman wavelength shifter 820. In addition, each selecting element 825a and 825b operates to at least partially reflect a desired wavelength to gain medium 824 to allow wavelength shifter 820 to continue lasing at the desired wavelength or wavelengths. In this particular embodiment, an optical cavity is formed between reflector 822 and selecting element 825a and/or selecting element 825b.

Figure 8C:
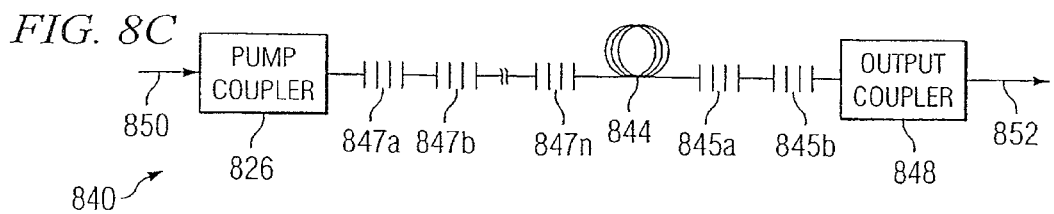

FIG. 8C is a block diagram illustrating one example of a Raman wavelength shifter 840 capable of shifting a shorter pump signal 850 wavelength to a longer output signal wavelength 852. In this example, Raman wavelength shifter 840 operates to generate an optical signal wavelength 852 of 1.7 microns or more. In various embodiments, Raman wavelength shifter 840 operates to generate an optical signal wavelength 852 in the mid-IR wavelength range. In other embodiments, Raman wavelength shifter 840 operates to generate an optical signal wavelength 852 a wavelength in the five (5) to seven (7) micron range. In various embodiments, pump signal 850 can comprise, for example, a 980 nanometer (nm) wavelength, a 1060 nm wavelength, a 1310 nm wavelength, a 1390 nm wavelength, a 1510 nm wavelength, or other optical signal wavelength.

In this example, Raman wavelength shifter 840 includes a gain fiber 844, a pump input coupler 846, and selecting elements 845. In various embodiments, the structure and function of gain fiber 844, coupler 826, selecting elements 845, and output coupler 848 can be substantially similar to gain fiber 824, coupler 826, selecting elements 825, and coupler 828 of FIG. 8B, respectively. In this particular embodiment, at least a portion of gain fiber 824 can comprise a chalcogenide fiber.

The example illustrated in FIG. 8C differs from the example illustrated in FIG. 8B in that wavelength shifter 840 implements a plurality of reflective gratings 847a-847n each centered on a different wavelength of a reflection band. Although this example includes three gratings, any number of gratings can be used without departing from the scope of the present disclosure. Gratings 847a-847n can comprise any device, such as a high-reflectivity dielectric grating. In this particular example, each grating 847a-847n comprises a grating with a reflectivity between ninety-five (95) to one hundred (100) percent at the center wavelength. Gratings 847a-847n operate to facilitate cascading of pump signal 850 to a desired output wavelength. In this particular embodiment, an optical cavity is formed between selecting elements 845 and gratings 847.

Figure 8D:
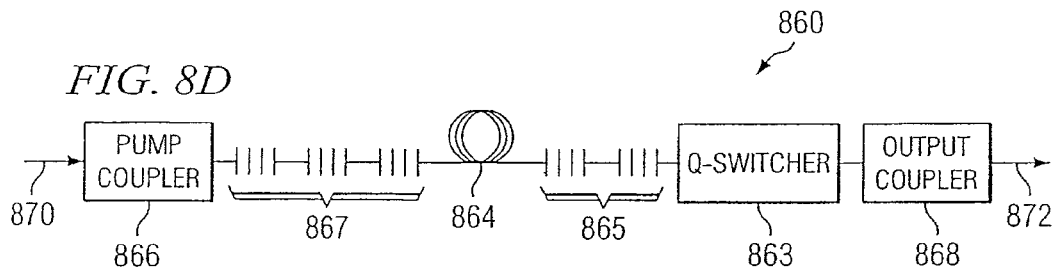

FIG. 8D is a block diagram illustrating one example of a Raman wavelength shifter 860 capable of shifting a shorter pump signal 870 wavelength to a longer output signal wavelength 832. In this example, Raman wavelength shifter 860 operates to generate an optical signal wavelength 872 of 1.7 microns or more. In various embodiments, Raman wavelength shifter 860 operates to generate an optical signal wavelength 872 in the mid-IR wavelength range. In other embodiments, Raman wavelength shifter 860 operates to generate an optical signal wavelength 872 a wavelength in the five (5) to seven (7) micron range. In various embodiments, pump signal 870 can comprise, for example, a 980 nm wavelength, a 1060 nm wavelength, a 1310 nm wavelength, a 1390 nm wavelength, a 1510 nm wavelength, or other optical signal wavelength.

In this example, Raman wavelength shifter 860 includes a gain fiber 864, a pump input coupler 866, electing elements 864, reflective gratings 867, and an output coupler 868. In various embodiments, the structure and function of gain fiber 864, input coupler 866, elements 864, gratings 867, and output coupler 868 can be substantially similar to gain fiber 844, coupler 846, elements 845, gratings 847, and coupler 848 of FIG. 8C, respectively. Although example elements are illustrated, Raman wavelength shifter 860 may include some, none, or all of these elements. For example, in some embodiments, pump input coupler 866 and/or output coupler 868 may be optional.

The example illustrated in FIG. 8D differs from the example illustrated in FIG. 8C in that wavelength shifter 860 implements a Q-switcher 863 capable of transitioning from a reflective state to a transmissive state. Q-switcher 863 can comprise a device or combination of devices having a variable loss. For example, Q-switcher may comprise one or more moving mirrors, electro-optic switches, saturable absorbers, or a combination of these or other optical devices. In some cases, Q-switcher 863 can initially operate as a reflective mirror so that optical signal energy may build-up within the laser cavity. After the laser cavity contains a sufficient amount of optical energy, Qswitcher 863 can operate to substantially transmit the desired optical signal wavelength in the form of a relatively large pulse or burst. In various embodiments, Q-switcher 863 may be capable of providing an output signal having a pulse width in the range of two (2) nanoseconds to one hundred (100) milliseconds. In other embodiments, Q-switcher 863 may be capable of providing an output signal having a pulse repetition rate in the range of two (2) hertz to one hundred (100) megahertz.

Figure 9A:
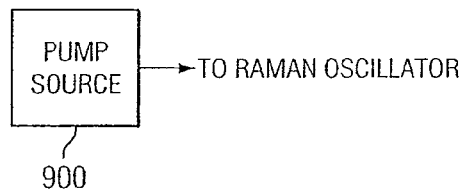
FIGS. 9A through 9C are block diagrams illustrating example embodiments of pump sources that are capable of generating a pump signal for use in a Raman wavelength shifter.
Figure 9B:
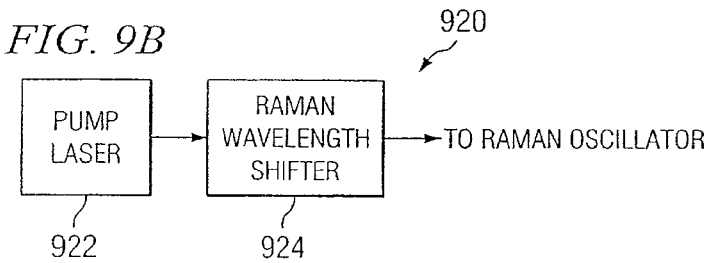
Figure 9C:
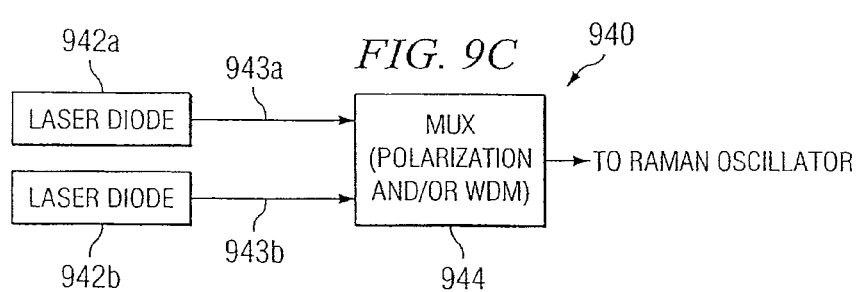

FIGS. 9A through 9C are block diagrams illustrating example embodiments of pump sources that are capable of generating a pump signal for use in a Raman wavelength shifter. Although particular examples of pump sources are described in FIGS. 9A through 9C, any other pump source can be implemented without departing from the scope of the present disclosure.

FIG. 9A is a block diagram illustrating one example embodiment of a pump source 900 capable of being coupled to a Raman wavelength shifter and/or a Raman oscillator. Pump source 900 can comprise any device capable of generating an optical signal at a desired wavelength and power. For example, pump source 900 can comprise a solid state laser, such a Nd:YAG or Nd:YLF laser, a semiconductor laser, a laser diode, a cladding pump fiber laser, or any combination of these or other light sources. In this example, pump source 900 comprises a high powered laser 902 coupled to a Raman oscillator or a Raman wavelength shifter, such as Raman wavelength shifters 800, 820, 840, or 860 of FIGS. 8A through 8D.

FIG. 9B is a block diagram illustrating one example embodiment of a pump source 920 capable of being coupled to a Raman wavelength shifter and/or a Raman oscillator. In this example, pump source 920 includes a pump laser 922 and an intermediate stage 924 capable of shifting the optical signal wavelength generated by pump laser 922 to a longer wavelength. The structure and function of laser 922 may be substantially similar to the structure and function of pump source 900 of FIG. 9A. In this particular example, intermediate state 924 comprises a first Raman wavelength shifter 924. In some embodiments, intermediate wavelength shifter 924 may advantageously be implemented using fused silica optical fiber.

In some embodiments, pump sources 900 and 920 may comprise a cladding-pumped fiber laser, capable of emitting a pump signal wavelength of approximately 1 micron. In those examples, pump sources 900 and 920 can be coupled to a first or auxiliary cascaded Raman oscillator or Raman wavelength shifter. In some cases, the auxiliary Raman oscillator or Raman wavelength shifter may comprise, for example, Raman wavelength shifters 800, 820, 840, or 860 of FIGS. 8A through 8D implementing a fused silica optical fiber. Such an arrangement may be used to shift the 1 micron optical signal to approximately 2 to 2.3 microns. The 2-2.3 micron signal output from the auxiliary Raman wavelength shifter can then be shifted to a mid-IR wavelength by another cascaded Raman oscillator or Raman wavelength shifter that implements in mid-IR fiber.

FIG. 9C is a block diagram illustrating one example embodiment of a pump source 940 capable of being coupled to a Raman wavelength shifter and/or a Raman oscillator. In this example, pump source 940 includes a pump laser 942 and a multiplexer 944 capable of combining a plurality of pump signals into a pump output signal. In this particular example, pump source 900 comprises a first laser diode 942a and a second laser diode 942b each centered at a desired wavelength and capable of generating pump signals 943a and 943b. Although this example includes two laser diodes, any number of laser diodes may be used without departing from the scope of the present disclosure. In various embodiments, laser diodes 942a and 942b can be centered on substantially the same wavelength, such as 980 nm, 1310 nm, 1390 nm, 14xx nm, or 1510 nm. In this particular embodiment, pump signals 943a and 943b are combined by multiplexer 944. Multiplexer 944 can comprise any device capable of combining pump signals 943, such as a wavelength division multiplexer. In various embodiments, multiplexer 944 can be capable of polarization and/or wavelength multiplexing pump signals 943a and 943b to form a pump output signal.

In some embodiments, a Raman wavelength shifter, such as those illustrated in FIGS. 8A through 8D, may be used to deliver an optical signal wavelength directly to the patient. In other embodiments, a second mid-IR waveguide structure, that at least partially transmits in at least a portion of the mid-IR wavelength range, may be coupled to the output of the Raman wavelength shifter to deliver the optical signal wavelength to the patient. Coupling a second mid-IR waveguide structure to the Raman wavelength shifter can advantageously allow the delivery waveguide structure to be disposed after use within the patient. In addition, coupling a second mid-IR waveguide structure can substantially reduce the chance of breaking a fiber associated with a Raman wavelength shifter. Furthermore, it may be desirable to couple a tapered end or lens on the delivery fiber for improved focusing of optical signal on the patient.

In various embodiments, an optical signal wavelength is capable of being delivered to a medical device inserted into a patient using a waveguide structure having a relatively low coupling loss. In some cases, the waveguide structure maintain the coupling loss to, for example, 5 dB or less, 3 dB or less, or even less than 1 dB.

Although the present invention has been described with several embodiments, a multitude of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A light-based medical diagnostic system, comprising:
a pump source comprising a plurality of semiconductor diodes with pump beams;
a multiplexer capable of combining the plurality of semiconductor diode pump beams and generating at least a multiplexed pump beam comprising one or more wavelengths;
a first waveguide structure configured to receive at least a portion of the one or more wavelengths, wherein the first waveguide structure comprises at least in part a gain fiber and outputs a first optical beam; and
a second waveguide structure configured to receive at least a portion of the first optical beam and to communicate at least the portion of the first optical beam to an output end of the second waveguide structure to form an output beam, wherein at least a portion of the output beam comprises at least one wavelength in the range of 1.7 microns or more; and
a lens system configured to receive at least the portion of the output beam and to communicate at least the portion of the output beam through a patient's mouth onto a part of a patient's body comprising a patient's blood;
wherein at least the portion of the output beam is adapted for use in medical diagnostics to measure a property of the patient's blood, wherein the medical diagnostics comprise a spectroscopic procedure comprising a differential measurement, wherein the differential measurement is based at least in part on a comparison of amplitudes at a plurality of associated wavelengths transmitted or reflected from the patient's blood.

2. The diagnostic system of claim 1, wherein the property of the patient's blood is blood pressure or blood oxygen level.

3. The diagnostic system of claim 1, wherein at least a portion of the first waveguide structure comprises a fused silica optical fiber, and wherein at least a portion of the second waveguide structure comprises a fused silica optical fiber.

4. The diagnostic system of claim 1, further comprising:
a processor configured to receive one or more signals from the differential measurement; and
a monitor in communication with the processor, wherein the monitor displays results from the processor based on the differential measurement.

5. The diagnostic system of claim 1, wherein the spectroscopic procedure is selected from the group consisting of transmission, reflection, fluorescence and microscopy.

6. A light-based diagnostic system, comprising:
- a pump source comprising a plurality of semiconductor diodes with pump beams;
- a multiplexer capable of combining the plurality of semiconductor diode pump beams and generating at least a multiplexed pump beam comprising one or more wavelengths;
- a first waveguide structure configured to receive at least a portion of the one or more wavelengths, wherein the first waveguide structure comprises at least in part a fused silica fiber, and outputs a first optical beam;
- a second waveguide structure configured to receive at least a portion of the first optical beam and to communicate at least the portion of the first optical beam to an output end of the second waveguide structure to form an output beam; and
- a lens system configured to receive at least a portion of the output beam and to communicate at least the portion of the output beam through an orifice in a patient's body;
- wherein at least the portion of the output beam is adapted for use in multi-wavelength diagnostics to measure a property of a part of the patient's body, wherein the multi-wavelength diagnostics comprise a spectroscopic procedure comprising a differential measurement, wherein the differential measurement is based at least in part on a comparison of amplitudes at a plurality of associated wavelengths transmitted or reflected from the part of the patient's body.

7. The diagnostic system of claim 6, wherein the orifice comprises a patient's mouth.

8. The diagnostic system of claim 6, wherein the property of the part of the patient's body comprises a property of a patient's blood.

9. The diagnostic system of claim 8, wherein the property of the patient's blood is blood pressure or blood oxygen level.

10. The diagnostic system of claim 6, wherein the spectroscopic procedure is selected from the group consisting of transmission, reflection, fluorescence and microscopy.

11. The diagnostic system of claim 6, further comprising:
- a processor configured to receive one or more signals from the differential measurement; and
- a monitor in communication with the processor, wherein the monitor displays results from the processor based on the differential measurement.

12. The diagnostic system of claim 6, wherein at least a portion of the first waveguide structure comprises a gain fiber and one or more optical gratings.

13. The diagnostic system of claim 6, wherein at least the portion of the output beam comprises at least one wavelength in the range of 1.7 microns or more.

14. The diagnostic system of claim 6, wherein the multi-wavelength diagnostics further comprise a blood sensor.

15. A light-based medical diagnostic system, comprising:
- a pump source comprising a plurality of semiconductor diodes with pump beams;
- a multiplexer capable of combining the plurality of semiconductor diode pump beams and generating at least a multiplexed pump beam comprising one or more wavelengths;
- a first waveguide structure configured to receive at least a portion of the one or more wavelengths, wherein the first waveguide structure comprises at least in part a fused silica fiber, and outputs a first optical beam;
- a second waveguide structure configured to receive at least a portion of the first optical beam and to communicate at least the portion of the first optical beam to an output end of the second waveguide structure to form an output beam; and
- a lens system configured to receive at least a portion of the output beam and to communicate at least the portion of the output beam onto a part of a patient's body comprising a patient's blood.

16. The diagnostic system of claim 15, wherein at least the portion of the output beam passes through an orifice in the patient's body.

17. The diagnostic system of claim 16, wherein the orifice comprises a patient's mouth.

18. The diagnostic system of claim 15, wherein at least the portion of the output beam comprises at least one wavelength in the range of 1.7 microns or more.

19. The diagnostic system of claim 15, wherein at least the portion of the output beam is adapted for use in medical diagnostics to measure a property of the patient's blood, wherein the medical diagnostics comprise a spectroscopic procedure comprising a differential measurement, wherein the differential measurement is based at least in part on a comparison of amplitudes at a plurality of associated wavelengths transmitted or reflected from the patient's blood.

20. The diagnostic system of claim 19, further comprising:
- a processor configured to receive one or more signals from the differential measurement; and
- a display in communication with the processor, wherein the display shows results from the processor based on the differential measurement.

* * * * *